United States Patent
Staudigel et al.

(10) Patent No.: US 8,980,239 B2
(45) Date of Patent: Mar. 17, 2015

(54) PERSONAL CARE COMPOSITIONS AND METHODS OF MAKING SAME

(71) Applicant: The Procter & Gamble Company, Cincinnati, OH (US)

(72) Inventors: James Anthony Staudigel, Loveland, OH (US); Eric Scott Johnson, Hamilton, OH (US); Sean Michael Renock, Loveland, OH (US); Marjorie Mossman Peffly, Cincinnati, OH (US); Kelly Rose Kroger Lyons, Blanchester, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 13/646,300

(22) Filed: Oct. 5, 2012

(65) Prior Publication Data

US 2013/0089587 A1  Apr. 11, 2013

Related U.S. Application Data

(60) Provisional application No. 61/544,769, filed on Oct. 7, 2011.

(51) Int. Cl.
*A61Q 5/00* (2006.01)
*A61K 8/06* (2006.01)
(Continued)

(52) U.S. Cl.
CPC ... *A61K 8/06* (2013.01); *A61Q 5/12* (2013.01); *A61K 8/891* (2013.01); *A61K 8/892* (2013.01);
(Continued)

(58) Field of Classification Search
None
See application file for complete search history.

(56) References Cited

U.S. PATENT DOCUMENTS 2,809,971 A  10/1957 Bernstein et al.
3,236,733 A  2/1966 Karsten et al.
(Continued)

FOREIGN PATENT DOCUMENTS

CN  101904908 A  12/2010
EP  0074819 A  3/1983
(Continued)

OTHER PUBLICATIONS

Engmann, J. et al. "Squeeze Flow Theory and Applications to Rheometry: A Review" J. of Non-Newtonian Fluid Mechanics, 132 (2005) 1-27.

(Continued)

*Primary Examiner* — Anand Desai
*Assistant Examiner* — Melissa Mercier
(74) *Attorney, Agent, or Firm* — Linda M. Sivik

(57) ABSTRACT

The present invention relates to a personal care composition and methods of using the same, the composition including an anionic surfactant, a cationic conditioning polymer, and a silicone emulsion wherein a total content of a cyclic polysiloxane having a general formula:

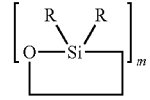

is present in the silicone emulsion in an amount less than 2.5 wt % based on the total weight of all polysiloxanes, R is a substituted or unsubstituted $C_1$ to $C_{10}$ alkyl or aryl, wherein m is 4 or 5, wherein the composition forms coacervate particles upon dilution with water, and wherein a percentage of the coacervate particles with a floc size of greater than about 20 micron is from about 1% to about 60% upon dilution with water.

20 Claims, 5 Drawing Sheets

(51) Int. Cl.

| | | |
|---|---|---|
| *A61Q 5/12* | (2006.01) | |
| *A61K 8/891* | (2006.01) | |
| *A61K 8/892* | (2006.01) | |
| *A61K 31/4164* | (2006.01) | |
| *A61K 31/4412* | (2006.01) | |
| *A61K 31/496* | (2006.01) | |
| *A61K 31/555* | (2006.01) | |
| *A61K 31/60* | (2006.01) | |
| *A61K 33/04* | (2006.01) | |
| *A61K 8/73* | (2006.01) | |
| *A61K 8/81* | (2006.01) | |

(52) U.S. Cl.
CPC ......... *A61K 31/4164* (2013.01); *A61K 31/4412* (2013.01); *A61K 31/496* (2013.01); *A61K 31/555* (2013.01); *A61K 31/60* (2013.01); *A61K 33/04* (2013.01); *A61K 8/737* (2013.01); *A61K 8/8158* (2013.01)
USPC ..................................................... 424/70.27

(56) References Cited

U.S. PATENT DOCUMENTS

| | | |
|---|---|---|
| 3,753,196 A | 8/1973 | Kurtz et al. |
| 3,761,418 A | 9/1973 | Parran |
| 4,323,683 A | 4/1982 | Bolich, Jr. et al. |
| 4,345,080 A | 8/1982 | Bolich, Jr. |
| 4,379,753 A | 4/1983 | Bolich, Jr. |
| 4,470,982 A | 9/1984 | Winkler |
| 5,104,646 A | 4/1992 | Bolich, Jr. et al. |
| 5,106,609 A | 4/1992 | Bolich, Jr. et al. |
| 5,723,112 A | 3/1998 | Bowser et al. |
| 8,435,501 B2 | 5/2013 | Peffly |
| 8,475,777 B2 | 7/2013 | Rautschek |
| 8,491,877 B2 * | 7/2013 | Schwartz et al. ............ 424/70.5 |
| 8,524,262 B2 | 9/2013 | Roy |
| 2002/0012646 A1 | 1/2002 | Royce |
| 2003/0108501 A1 * | 6/2003 | Hofrichter et al. ........... 424/70.1 |
| 2003/0176303 A1 | 9/2003 | Niemiec et al. |
| 2004/0157755 A1 | 8/2004 | Niemiec et al. |
| 2004/0234484 A1 | 11/2004 | Peffly |
| 2007/0276087 A1 | 11/2007 | Paul et al. |
| 2008/0206179 A1 | 8/2008 | Peffly et al. |
| 2008/0206355 A1 | 8/2008 | Schwartz et al. |
| 2009/0176674 A1 | 7/2009 | Peffly et al. |
| 2011/0002868 A1 | 1/2011 | Bierganns et al. |
| 2013/0089586 A1 | 4/2013 | Johnson |

FOREIGN PATENT DOCUMENTS

| | | |
|---|---|---|
| EP | 0136914 A | 4/1985 |
| EP | 1080714 A2 | 3/2001 |
| EP | 1437121 A1 | 7/2004 |
| WO | 9966886 A | 6/1998 |
| WO | 03105793 A2 | 12/2003 |
| WO | 2010080167 A2 | 7/2010 |
| WO | 2012095374 | 7/2012 |
| WO | 2013050241 A1 | 4/2013 |

OTHER PUBLICATIONS

Lepilleur, Carole, et al. "Use of Statistical modeling to predict the effect of formulation composition on coacervation, silicone deposition, and conditioning sensory performance of Cationic Cassia Polymers" J. Cosmet Sci., 62, 161-177.

Morioka, H., Tagaya, H., Karasu, M, Kadokawa, J, Chiba, K "Effects of Zinc on the New Preparation Method of Hydroxy Double Salts" Inorg. Chem. 1999, 38, 4211-6.

International Search Report PCT/US2012/058990; Mailing Date Nov. 7, 2013; 13 pages.

International Search Report PCT/US2012/058909; Mailing Date Nov. 7, 2013; 13 pages.

* cited by examiner

PERSONAL CARE COMPOSITIONS AND METHODS OF MAKING SAME

FIELD OF THE INVENTION

The present invention relates to a personal care composition and methods of making same. More specifically, it relates to a personal care composition including an anionic surfactant, a cationic conditioning polymer, and a silicone emulsion.

BACKGROUND OF THE INVENTION

Conditioning shampoos or "2 in 1" hair products comprising a detersive surfactant and hair conditioning agents are known. These personal care compositions typically comprise an anionic detersive surfactant in combination with a conditioning agent such as a silicone, hydrocarbon oil, fatty esters, etc. These products have become more popular among consumers as a means of conveniently obtaining hair conditioning and cleansing performance from a single product.

Many conditioning personal care compositions, however, do not provide sufficient deposition of conditioning agents onto hair or skin during the application process and if deposition is possible, it is only possible in formulations with relatively low levels of anionic surfactant. Without adequate deposition, large proportions of conditioning agent are rinsed away during the application process and therefore provide little or no conditioning benefit. Without sufficient deposition of the conditioning agent on the hair or skin, relatively high levels of conditioning agents may be needed. Such high levels of a conditioning agent, however, can increase raw material costs, reduce lathering, and present product stability concerns. Additionally, limitations on total anionic surfactant in order to form coacervate can limit the lather potential of a composition, or result in the need for higher levels of less cost effective amphoteric surfactants in order to achieve good lather.

One known method for improving deposition of a hair conditioning agent onto hair involves the use of specific cationic deposition polymers. These polymers may be synthetic, but are most commonly natural cellulosic or guar polymers that have been modified with cationic substituents.

The formation of a coacervate upon dilution of the cleansing composition with water is important to improving deposition of various conditioning actives, especially those that have small droplet sizes (i.e., ≤2 microns). In order to form a coacervate, cleansing compositions comprising typical cationic polymers tend to be significantly limited in total anionic surfactant concentrations, in order to achieve adequate levels of coacervate particles upon dilution. However, lower levels of anionic surfactants tend to limit the volume of lather that can be achieved with a particular cleansing composition. Thus, for cost effective, high lathering, coacervate-forming compositions, it is desirable to use a cationic polymer that can form a coacervate in the presence of high levels of anionic surfactant.

But another complexity arises when the composition comprises an active substance, such as an anti-dandruff active, which also needs to be deposited on the scalp in an efficacious deposition amount and quality. However, excellent deposition amount and quality of active substances, for example by utilizing high levels of cationic polymers and those with higher charge density, is often associated with a hair conditioning feel that many consumers find unacceptable.

Consequently, needs exist for a conditioning composition that provides excellent active substance deposition performance without a hair conditioning and hair feel trade-off.

SUMMARY OF THE INVENTION

These and other features, aspects, and advantages of the claimed invention will become evident to those skilled in the art from a reading of the present disclosure.

In accordance with an embodiment of the present invention, a personal care composition is provided. The composition comprises a) an anionic surfactant; b) a cationic conditioning polymer; and a silicone emulsion. The cationic conditioning polymer is selected from at least one of i) a cationic guar polymer, wherein the cationic guar polymer has a weight average molecular weight of less than about 1 million g/mol, and wherein the cationic guar polymer has a charge density of from about 0.1 meq/g to about 2.5 meq/g; or ii) a cationic copolymer of an acrylamide monomer and a cationic monomer, wherein the copolymer has a charge density of from about 1.0 meq/g to about 3.0 meq/g. The silicone emulsion comprises an insoluble polysiloxane having a general formula of $R^1$—[O—$SiR_2$]$_n$—$OR^1$, wherein n is an integer, R is a substituted or unsubstituted $C_1$ to $C_{10}$ alkyl or aryl, and $R^1$ is a hydrogen or a substituted or unsubstituted $C_1$ to $C_{10}$ alkyl or aryl, wherein the insoluble polysiloxane has an average molecular weight within the range from about 50,000 to about 500,000 g/mol, and an average particle size within the range from about 30 nm to about 10 μm, wherein a total content of a cyclic polysiloxane having a general formula:

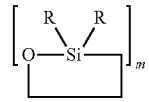

is present in the silicone emulsion in an amount less than about 2.5 wt % based on the total weight of the insoluble polysiloxane and the cyclic polysiloxane, wherein R is as defined above, wherein m is 4 or 5, and wherein the composition forms coacervate particles upon dilution with water, and wherein a percentage of the coacervate particles with a floc size of greater than about 20 micron is from about 1% to about 60% upon dilution with water.

According to another embodiment of the present invention, a method of achieving improved hair feel is provided. The method comprises applying to hair a composition comprising: a) an anionic surfactant; b) a cationic conditioning polymer; and c) a silicone emulsion. The cationic conditioning polymer is selected from at least one of i) a cationic guar polymer, wherein the cationic guar polymer has a weight average molecular weight of less than about 1 million g/mol, and wherein the cationic guar polymer has a charge density of from about 0.1 meq/g to about 2.5 meq/g; or ii) a cationic copolymer of an acrylamide monomer and a cationic monomer, wherein the copolymer has a charge density of from about 1.0 meq/g to about 3.0 meq/g. The silicone emulsion comprises an insoluble polysiloxane having a general formula of $R^1$—[O—$SiR_2$]$_n$—$OR^1$, wherein n is an integer, R is a substituted or unsubstituted $C_1$ to $C_{10}$ alkyl or aryl, and $R^1$ is a hydrogen or a substituted or unsubstituted $C_1$ to $C_{10}$ alkyl or aryl, wherein the insoluble polysiloxane has an average molecular weight within the range from about 50,000 to about 500,000 g/mol, and an average particle size within the range from about 30 nm to about 10 μm, and wherein a total content of a cyclic polysiloxane having a general formula:

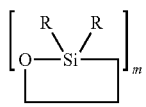

is present in the silicone emulsion in an amount less than 2.5 wt % based on the total weight of the insoluble polysiloxanes and the cyclic polysiloxane, R is as defined above, wherein m is 4 or 5, wherein the composition forms coacervate particles upon dilution with water, wherein the coacervate particles have a squeeze flow viscosity of from about 1 Pa·s to about 100 Pa·s, and wherein a percentage of the coacervate particles with a floc size of greater than about 20 micron is from about 1% to about 60%.

According to another embodiment of the present invention, a method of making a personal care composition comprising an anionic surfactant, a cationic conditioning polymer, and a silicone emulsion is provided, The method comprises (a) combining the anionic surfactant and the cationic conditioning polymer in water, wherein the cationic conditioning polymer is selected from at least one of (i) a cationic guar polymer, wherein the cationic guar polymer has a weight average molecular weight of less than about 1 million g/mol, and wherein the cationic guar polymer has a charge density of from about 0.1 meq/g to about 2.5 meq/g; or (b) a cationic copolymer of an acrylamide monomer and a cationic monomer, wherein the copolymer has a charge density of from about 1 meq/g to about 3 meq/g; and (ii) combining a silicone emulsion and an aqueous composition that includes a product of step (i) to form the personal care composition, the silicone emulsion comprising an insoluble polysiloxane having a general formula of $R^1$—[O—$SiR_2$]$_n$—$OR^1$, wherein n is an integer, R is a substituted or unsubstituted $C_1$ to $C_{10}$ alkyl or aryl, and $R^1$ is a hydrogen or a substituted or unsubstituted $C_1$ to $C_{10}$ alkyl or aryl, wherein the insoluble polysiloxane has an average molecular weight within the range from about 50,000 to about 500,000 g/mol, and an average particle size within the range from about 30 nm to about 10 μm, and wherein a total content of a cyclic polysiloxane having a general formula

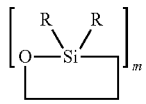

is present in the silicone emulsion in an amount less than 2.5 wt % based on the total weight of the insoluble polysiloxanes and the cyclic polysiloxane, wherein R is as defined above, wherein m is 4 or 5, and wherein the composition forms coacervate particles upon dilution with water, wherein the coacervate particles have a squeeze flow viscosity of from about 1 Pa·s to about 100 Pa·s, and wherein a percentage of the coacervate particles with a floc size of greater than about 20 micron is from about 1% to about 60%.

DETAILED DESCRIPTION OF THE INVENTION

Figure 1:
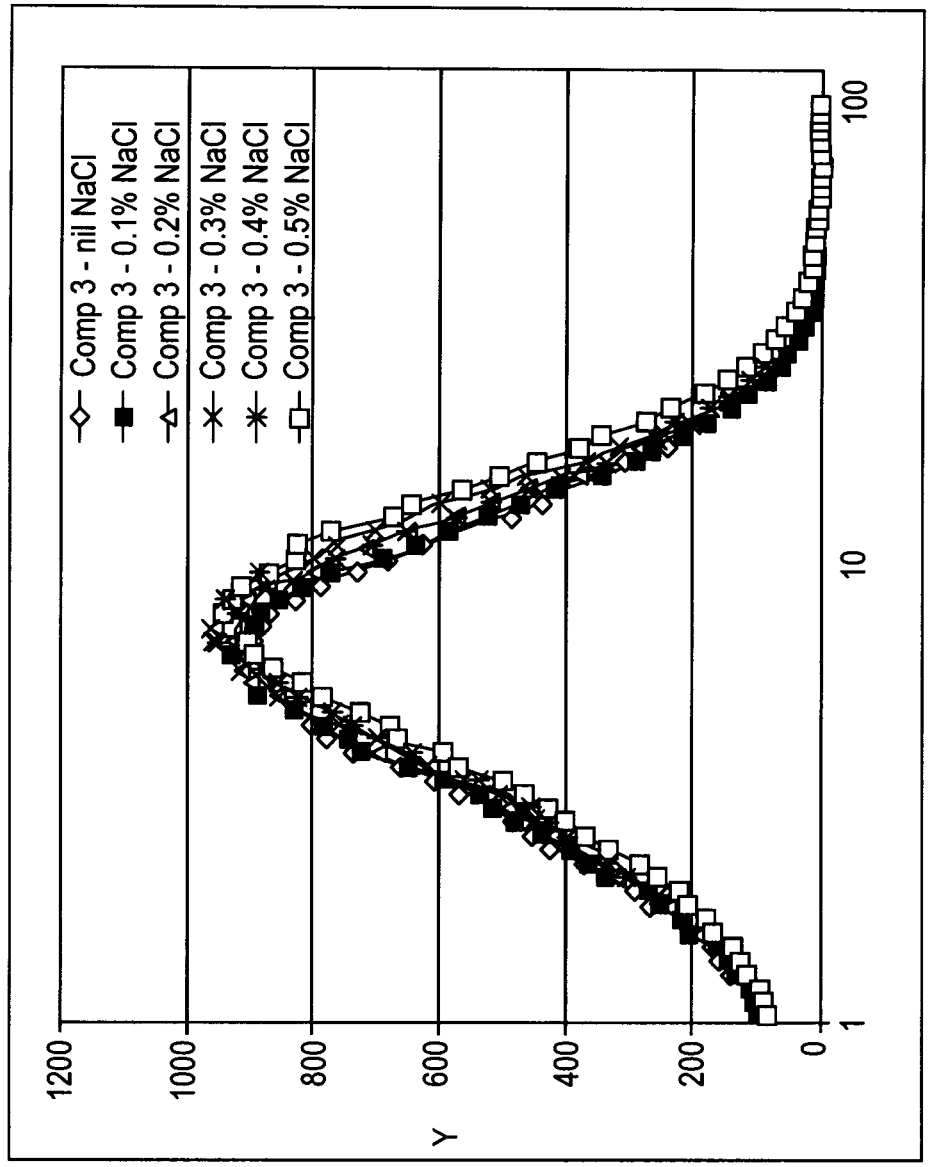
FIG. 1 is a graphical representation showing the effect of salt concentration on a floc size of a coacervate of a personal care composition in accordance with one embodiment of the present invention.

All percentages are by weight of the total composition, unless stated otherwise. All ratios are weight ratios, unless specifically stated otherwise. All ranges are inclusive and combinable. The number of significant digits conveys neither a limitation on the indicated amounts nor on the accuracy of the measurements. The term "molecular weight" or "M.Wt." as used herein refers to the weight average molecular weight unless otherwise stated. "QS" means sufficient quantity for 100%.

All numerical amounts are understood to be modified by the word "about" unless otherwise specifically indicated. Unless otherwise indicated, all measurements are understood to be made at 25° C. and at ambient conditions, where "ambient conditions" means conditions under about one atmosphere of pressure and at about 50% relative humidity. All such weights as they pertain to listed ingredients are based on the active level and do not include carriers or by-products that may be included in commercially available materials, unless otherwise specified.

Herein, "comprising" means that other steps and other ingredients which do not affect the end result can be added. This term encompasses the terms "consisting of" and "consisting essentially of". The compositions, methods, uses, kits, and processes of the present invention can comprise, consist of, and consist essentially of the elements and limitations of the invention described herein, as well as any of the additional or optional ingredients, components, steps, or limitations described herein.

The term "substantially free from" or "substantially free of" as used herein means less than about 1%, or less than about 0.8%, or less than about 0.5%, or less than about 0.3%, or about 0%, by total weight of the composition.

"Hair," as used herein, means mammalian hair including scalp hair, facial hair and body hair, particularly on hair on the human head and scalp.

"Cosmetically acceptable," as used herein, means that the compositions, formulations or components described are suitable for use in contact with human keratinous tissue without undue toxicity, incompatibility, instability, allergic response, and the like. All compositions described herein which have the purpose of being directly applied to keratinous tissue are limited to those being cosmetically acceptable.

"Derivatives," as used herein, includes but is not limited to, amide, ether, ester, amino, carboxyl, acetyl, acid, and/or alcohol derivatives of a given compound.

"Polymer," as used herein, means a chemical formed from the polymerisation of two or more monomers. The term "polymer" as used herein shall include all materials made by the polymerisation of monomers as well as natural polymers. Polymers made from only one type of monomer are called homopolymers. A polymer comprises at least two monomers. Polymers made from two or more different types of monomers are called copolymers. The distribution of the different monomers can be calculated statistically or block-wise—both possibilities are suitable for the present invention. Except if stated otherwise, the term "polymer" used herein includes any type of polymer including homopolymers and copolymers.

"Kit," as used herein, means a packaging unit comprising a plurality of components. An example of a kit is, for example, a first composition and a separately packaged second composition. Another kit may comprise a first composition and an energy delivery device. A different kit may comprise three different types of separately packaged composition and a hair styling implement. A further kit may comprise application instructions comprising a method and a composition/formulation.

The term "coacervate" as used herein, means the complex which forms between surfactant and polymer that may either be soluble or insoluble in the neat personal care composition, typically forming an insoluble complex in the neat personal care composition, and which may become less soluble upon dilution and thus yielding an increase in its level of phase separation or precipitate in solution.

The term "floc" as used herein, means localized clusters of agglomerated, insoluble coacervate, which may comprise polymer, surfactant, water and dispersed phases present in the composition such as anti-dandruff active and silicone emulsion. Any floc size disclosed herein is obtained using a Lasentec Focused Beam Reflectance Measurment (FBRM) [model S400A available from Mettler Toledo Corp.] in accordance with the Lasentec Method, which is described below.

The term "isotropic" as used herein, means a particular phase structure of coacervate wherein the structure is "identical along any three orthogonal directions in space, and is therefore dark or 'nonbirefringent' when viewed between crossed polarized light. (One direction is 'orthogonal' to another if the vector component of the first, in the direction of the second, is zero.)" (Laughlin, R. G. (1994). "The Aqueous Phase Behavior of Surfactants," 182, 8.2).

The term "charge density" as used herein, means the ratio of the number of positive charges on a monomeric unit of which a polymer is comprised to the M.Wt. of said monomeric unit. The charge density multiplied by the polymer M.Wt. determines the number of positively charged sites on a given polymer chain. For cationic guars, charge density is measured using standard elemental analysis of percentage nitrogen known to one skilled in the art. This value of percentage nitrogen, corrected for total protein analysis, can then be used to calculate the number or equivalence of positive charges per gram of polymer. For the cationic copolymers, the charge density is a function of the monomers used in the synthesis. Standard NMR techniques know to one skilled in the art would be used to confirm that ratio of cationic and non-ionic monomers in the polymer. This would then be used to calculate the number or equivalence of positive charges per gram of polymer. Once these values are know, the charge density is reported in milliequivalence (meq) per gram of cationic polymer.

The term "(meth)acrylamide" as used herein means methylacrylamide or acrylamide. The term "(meth)acrylic acid" as used herein means acrylic acid or methacrylic acid.

In accordance with embodiments of the present invention, a personal care composition is provided, the composition including an anionic surfactant, a cationic conditioning polymer, and a silicone emulsion including an insoluble polysiloxane.

It has been surprisingly found that, by formulating personal care composition with a silicone emulsion of an insoluble polysiloxane, e.g., poly-dimethylsiloxane, having at total content of cyclic polysiloxane of less than 2.5 wt % based on the total weight of all polysiloxanes, in combination with cationic guar polymers and/or cationic copolymers of acrylamide monomers and cationic monomers, improves the deposition of the conditioning polymer and the insoluble polysiloxane on the skin and hair can be improved with minimal or no consumer unacceptance of hair conditioning and hair feel.

Figure 2:
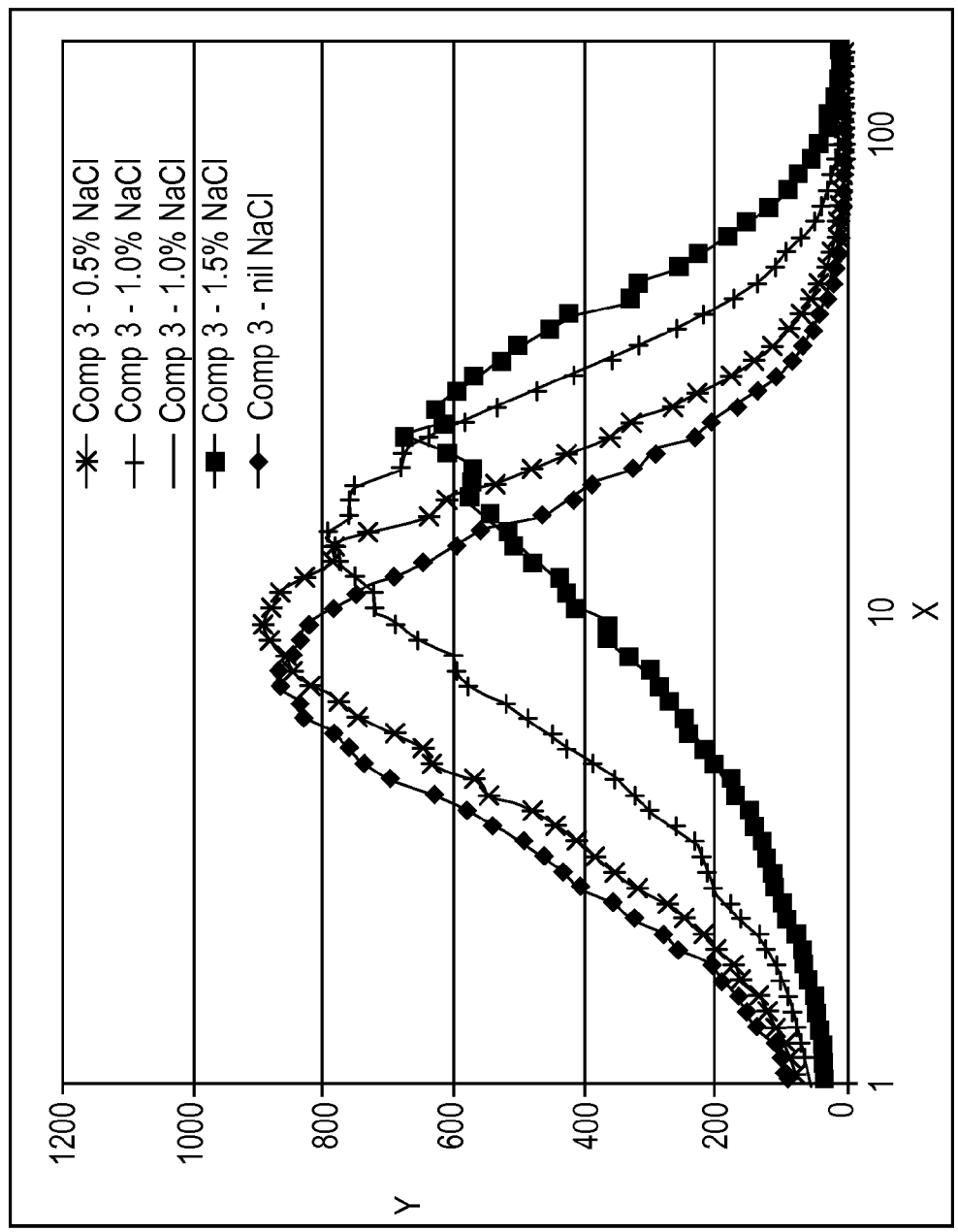
FIG. 2 is a graphical representation showing the effect of salt concentration on a floc size of a coacervate of a personal care composition in accordance with another embodiment of the present invention.

Without being bound by any particular theory, it is believed that insoluble polysiloxanes emulsions having levels of cyclic polysiloxanes below the aforementioned threshold, provide improved consumer acceptance of hair conditioning and hair feel and yet also excellent on-scalp deposition. It is believed that cyclic polysiloxanes disrupt higher order surfactant micelle formation, which in turn requires increasing the amount of salt to be added to the composition in order to achieve acceptable rheology parameters of the composition. However, the observed increase in viscosity induced by the increased salt content may also be associated with an increased floc size of the coacervate, as shown in FIGS. 1 and 2. Increasing floc size can negatively affect the on-scalp deposition, for example, by a larger floc becoming trapped in the hair. By blending an anionic surfactant, a cationic conditioning polymer, and the silicone emulsion defined herein, it has been surprisingly found that both the consumer desirable benefits of the lower molecular weight cationic guars and the enhanced deposition of the cationic copolymers and silicone can be achieved in a single composition while still preserving the consumer desirability. Advantageously, this combination of surfactant, polymer and silicone is useful for the deposition of actives, such as anti-dandruff actives.

More specifically, it is believed that an insoluble polysiloxane of a desired particle size (<10 micron) in the embodiments of the present invention can be delivered to the hair and scalp via entrapment in the coacervate microstructure. Insoluble polysiloxane species entrapped in the coacervate microstructure result in a less tightly bound structure which can be characteristic of high deposition systems like cationic guar/synthetic co-polymer systems. Less tightly bound coacervate microstructures can be characterized by reduced complex coacervate rheology (CCR).

The impact of the silicone emulsion further dictates the achievement of the desired reduction of coacervate floc size and rheology. In general, silicone microemulsions and nanoemulsions contain various amounts of residual cyclic polysiloxanes. For example, dimethiconol may include significant quantities of cyclic polysiloxanes, such as octamethylcyclotetrasiloxane and decamethylcyclotetrasiloxane. The cyclic polysiloxanes can significantly impact anionic surfactant based compositions, such as shampoos, by disrupting higher order surfactant micelle formation, which is critical for achieving consumer accepted compositional viscosity targets. As a consequence of the higher order micelle formation disruption, higher levels of NaCl are added to the personal care composition in order to compensate for the drop in viscosity. However, increasing the salt level produces a larger coacervate particle size, which has been shown to result in a negative cosmetic experience. Accordingly, silicone emulsions of polysiloxanes with cyclic polysiloxanes below specified levels unexpectedly yield excellent deposition and quality, while providing improved hair feel.

The features of the composition according to the first aspect, as well as the other aspects and other relevant components, are described in detail hereinafter. All components of the composition described herein should be physically and chemically compatible with the essential components described herein, and should not otherwise unduly impair product stability, aesthetics or performance.

In accordance with one embodiment of the present invention, a personal care composition is provided, comprising: a) an anionic surfactant; b) a cationic conditioning polymer; and c) a silicone emulsion comprising an insoluble polysiloxane.

A. Silicone Emulsion

The silicone emulsions suitable for use in the embodiments of the present invention include emulsions of insoluble polysiloxanes prepared in accordance with the descriptions provided in U.S. Pat. No. 4,476,282 and U.S. Patent Application Publication No. 2007/0276087. Accordingly, insoluble polysiloxanes referred to herein for the purpose of the invention include polysiloxanes such as alpha, omega hydroxy-terminated polysiloxanes or alpha, omega alkoxy-terminated polysiloxanes having a molecular weight within the range from about 50,000 to about 500,000 g/mol. As used herein, "insoluble polysiloxane" means that the water solubility of the polysiloxane is less than 0.05 wt %. In another embodiment, the water solubility of the polysiloxane is less than 0.02 wt %, or less than 0.01 wt %, or less than 0.001 wt %. According to an embodiment, the insoluble polysiloxane is present in the personal care composition in an amount within the range from about 0.1 wt % to about 3 wt %, based on the total weight of the composition. For example, the insoluble polysiloxane can be present in an amount within the range from about 0.2 wt % to about 2.5 wt %, or from about 0.4 wt % to about 2.0 wt %, or from about 0.5 wt % to about 1.5 wt %, based on the total weight of the composition.

According to one aspect of the silicone emulsion, the insoluble polysiloxane used herein include alpha, omega hydroxy- or alkoxy-terminated polysiloxanes having a general formula I:

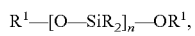

wherein 'n' is an integer, R is a substituted or unsubstituted $C_1$ to $C_{10}$ alkyl or aryl, and $R^1$ is a hydrogen or a substituted or unsubstituted $C_1$ to $C_{10}$ alkyl or aryl. Non-limiting examples of R and $R^1$ may be independently selected from alkyl groups such as methyl, ethyl, n-propyl, isopropyl, n-butyl, isobutyl, tert-butyl, n-pentyl, isopentyl, neopentyl, tertpentyl, hexyl such as n-hexyl, heptyl such as n-heptyl, octyl such as n-octyl and isooctyl such as 2,2,4-trimethyl-pentyl, nonyl such as n-nonyl, decyl such as n-decyl, dodecyl such as n-dodecyl, octadecyl such as n-octadecyl; or aryl groups such as phenyl, naphthyl, anthryl and phenanthryl. In an embodiment, the insoluble polysiloxane has a general formula H—[O—SiR$_2$]$_n$—OH.

According to another aspect of the silicone emulsion, the insoluble polysiloxane has an average molecular weight within the range from about 50,000 to about 500,000 g/mol. For example, the insoluble polysiloxane may have an average molecular weight within the range from about 60,000 to about 400,000; from about 75,000 to about 300,000; from about 100,000 to about 200,000; or the average molecular weight may be about 150,000 g/mol.

According to another aspect of the silicon emulsion, total content of a cyclic polysiloxane having a general formula:

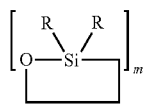

wherein R is as defined above, and wherein m is 4 or 5, is present in the silicone emulsion in an amount less than about 2.5 wt % based on the total weight of all polysiloxanes. For example, dimethiconol may include significant quantities of cyclic polysiloxanes, such as octamethylcyclotetrasiloxane (D4) and decamethylcyclotetrasiloxane (D5). In an embodiment, the amount of D4 is less than about 2.0%, or less than about 1.5%, or less than about 1.0%, or less than about 0.5%, based on the total weight of all polysiloxanes. In an embodiment, the amount of D5 is less than about 0.5%, or less than about 0.4%, or less than about 0.3%, or less than about 0.2%, based on the total weight of all polysiloxanes.

According to yet another aspect of the silicone emulsion, the emulsion has a viscosity up to about 500,000 cPs. For example, the viscosity may be within the range from about 75,000 to about 300,000, from about 100,000 to about 200,000, or about 150,000 cPs.

According to yet another aspect of the silicone emulsion, the insoluble polysiloxane has an average particle size within the range from about 30 nm to about 10 micron. The average particle size may be within the range from about 40 nm to about 5 micron, from about 50 nm to about 1 micron, from about 75 nm to about 500 nm, or about 100 nm, for example.

The average molecular weight of the insoluble polysiloxane, the viscosity of the silicone emulsion, and the size of the particle comprising the insoluble polysiloxane are determined by methods commonly used by those skilled in the art, such as the methods disclosed in Smith, A. L. *The Analytical Chemistry of Silicones*, John Wiley & Sons, Inc.: New York, 1991. For example, the viscosity of the silicone emulsion can be measured at 30° C. with a Brookfield viscosimeter with spindle 6 at 2.5 rpm.

According to another aspect of the silicone emulsion, the emulsion further includes an anionic surfactant that participates in providing high internal phase viscosity emulsions having particle sizes in the range from about 30 nm to about 10 micron. The anionic surfactant is selected from organic sulfonic acids. Most common sulfonic acids used in the present process are alkylaryl sulfonic acid; alkylaryl polyoxyethylene sulphonic acid; alkyl sulfonic acid; and alkyl polyoxyethylene sulfonic acid. General formulas of the sulfonic acids are as shown below:

 (II)

 (III)

 (IV)

 (IV)

Where $R^2$, which may differ, is a monovalent hydrocarbon radical having at least 6 carbon atoms. Non-limiting examples of $R^2$ include hexyl, octyl, decyl, dodecyl, cetyl, stearyl, myristyl, and oleyl. 'm' is an integer from 1 to 25. Exemplary anionic surfactants include but are not limited to octylbenzene sulfonic acid; dodecylbenzene sulfonic acid; cetylbenzene sulfonic acid; alpha-octyl sulfonic acid; alpha-dodecyl sulfonic acid; alpha-cetyl sulfonic acid; polyoxyethylene octylbenzene sulfonic acid; polyoxyethylene dodecylbenzene sulfonic acid; polyoxyethylene cetylbenzene sulfonic acid; polyoxyethylene octyl sulfonic acid; polyoxyethylene dodecyl sulfonic acid; and polyoxyethylene cetyl sulfonic acid. Generally, 1 to 15% anionic surfactant is used in the emulsion process. For example, 3-10% anionic surfactant can be used to obtain an optimum result.

The silicone emulsion may further include an additional emulsifier together with the anionic surfactant, which along with the controlled temperature of emulsification and polymerization, facilitates making the emulsion in a simple and faster way. Non-ionic emulsifiers having a hydrophilic lipophilic balance (HLB) value of 10 to 19 are suitable and include polyoxyalkylene alkyl ether, polyoxyalkylene alkylphenyl ethers and polyoxyalkylene sorbitan esters. Some useful emulsifiers having an HLB value of 10 to 19 include, but are not limited to, polyethylene glycol octyl ether; polyethylene glycol lauryl ether; polyethylene glycol tridecyl ether; polyethylene glycol cetyl ether; polyethylene glycol stearyl ether; polyethylene glycol nonylphenyl ether; polyethylene glycol dodecylphenyl ether; polyethylene glycol cetylphenyl ether; polyethylene glycol stearylphenyl ether; polyethylene glycol sorbitan mono stearate; and polyethylene glycol sorbitan mono oleate.

B. Cationic Conditioning Polymers

According to another aspect of embodiments of the present inventions, the cationic conditioning polymer includes at least one of (a) a cationic guar polymer or (b) a cationic copolymer of acrylamide monomers and cationic monomers.

(a) Cationic Guar Polymers

According to an embodiment of the present invention, the personal care composition comprises a cationic guar polymer, which is a cationically substituted galactomannan (guar) gum derivatives. Guar gum for use in preparing these guar gum derivatives is typically obtained as a naturally occurring material from the seeds of the guar plant. The guar molecule itself is a straight chain mannan, which is branched at regular intervals with single membered galactose units on alternative mannose units. The mannose units are linked to each other by means of $\beta(1\text{-}4)$ glycosidic linkages. The galactose branching arises by way of an $\alpha(1\text{-}6)$ linkage. Cationic derivatives of the guar gums are obtained by reaction between the hydroxyl groups of the polygalactomannan and reactive quaternary ammonium compounds. The degree of substitution of the cationic groups onto the guar structure must be sufficient to provide the requisite cationic charge density described above.

According to one embodiment, the cationic guar polymer has a weight average M.Wt. of less than about 1 million g/mol, and has a charge density of from about 0.1 meq/g to about 2.5 meq/g. In an embodiment, the cationic guar polymer has a weight average M.Wt. of less than 900 thousand g/mol, or from about 150 thousand to about 800 thousand g/mol, or from about 200 thousand to about 700 thousand g/mol, or from about 300 thousand to about 700 thousand g/mol, or from about 400 thousand to about 600 thousand g/mol. from about 150 thousand to about 800 thousand g/mol, or from about 200 thousand to about 700 thousand g/mol, or from about 300 thousand to about 700 thousand g/mol, or from about 400 thousand to about 600 thousand g/mol. In one embodiment, the cationic guar polymer has a charge density of from about 0.2 to about 2.2 meq/g, or from about 0.3 to about 2.0 meq/g, or from about 0.4 to about 1.8 meq/g; or from about 0.5 meq/g to about 1.5 meq/g.

In an embodiment, the composition comprises from about 0.01% to less than about 0.6%, or from about 0.04% to about 0.55%, or from about 0.08% to about 0.5%, or from about 0.16% to about 0.5%, or from about 0.2% to about 0.5%, or from about 0.3% to about 0.5%, or from about 0.4% to about 0.5%, of cationic guar polymer (a), by total weight of the composition.

The cationic guar polymer may be formed from quaternary ammonium compounds. In an embodiment, the quaternary ammonium compounds for forming the cationic guar polymer conform to the general formula:

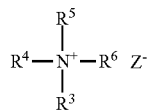

wherein where $R^3$, $R^4$ and $R^5$ are methyl or ethyl groups; R is 6 either an epoxyalkyl group of the general formula:

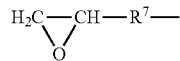

or $R^6$ is a halohydrin group of the general formula:

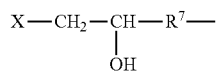

wherein $R^7$ is a $C_1$ to $C_3$ alkylene; X is chlorine or bromine, and Z is an anion such as Cl—, Br—, I— or $HSO_4$—.

In an embodiment, the cationic guar polymer conforms to the general formula:

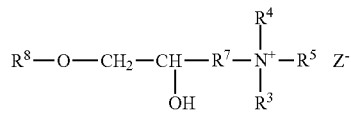

wherein $R^8$ is guar gum; and wherein $R^4$, $R^5$, $R^6$ and $R^7$ are as defined above; and wherein Z is a halogen. In an embodiment, the cationic guar polymer conforms to Formula G:

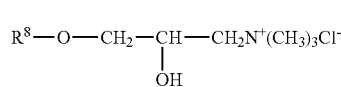

Formula G

Suitable cationic guar polymers include cationic guar gum derivatives, such as guar hydroxypropyltrimonium chloride. In an embodiment, the cationic guar polymer is a guar hydroxypropyltrimonium chloride. Specific examples of guar hydroxypropyltrimonium chlorides include the Jaguar® series commercially available from Rhone-Poulenc Incorporated, for example Jaguar® C-500, commercially available from Rhodia. Jaguar® C-500 has a charge density of 0.8 meq/g and a M.Wt. of 500,000 g/mole. Another guar hydroxypropyltrimonium chloride with a charge density of about 1.1 meq/g and a M.Wt. of about 500,000 g/mole is available from Ashland. A further guar hydroxypropyltrimonium chloride with a charge density of about 1.5 meq/g and a M.Wt. of about 500,000 g/mole is available from Ashland.

Jaguar® C-17 is not suitable as the cationic guar polymer (a) for the present invention. Jaguar® C-17 conforms to Formula G and has a cationic charge density of about 0.6 meq/g and a M.Wt. of about 2.2 million g/mol and is available from Rhodia Company. Jaguar® C 13S is also not suitable for the present invention since, although it conforms to Formula G, it has a M.Wt. of 2.2 million g/mol and a cationic charge density of about 0.8 meq/g (available from Rhodia Company). In an embodiment, the present invention is substantially free of Jaguar® C-17 and/or Jaguar® C 13S.

Other suitable polymers include: Hi-Care 1000, which has a charge density of about 0.7 meq/g and a M.Wt. of about 600,000 g/mole and is available from Rhodia; N-Hance 3269 and N-Hance 3270, which have a charge density of about 0.7 meq/g and a M.Wt. of about 425,000 g/mole and is available from Ashland; AquaCat CG518 has a charge density of about 0.9 meq/g and a M.Wt. of about 50,000 g/mole and is available from Ashland.

(ii) Cationic Copolymers

According to an embodiment of the present invention, the personal care composition comprises (b) a cationic copolymer of an acrylamide monomer and a cationic monomer, wherein the copolymer has a charge density of from about 1.0 meq/g to about 3.0 meq/g. In an embodiment, the cationic copolymer is a synthetic cationic copolymer of acrylamide monomers and cationic monomers.

In an embodiment, the cationic copolymer comprises:
(i) an acrylamide monomer of the following Formula AM:

Formula AM

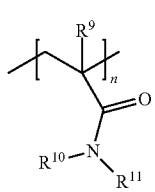

where $R^9$ is H or $C_{1-4}$ alkyl; and $R^{10}$ and $R^{11}$ are independently selected from the group consisting of H, $C_{1-4}$ alkyl, $CH_2OCH_3$, $CH_2OCH_2CH(CH_3)_2$, and phenyl, or together are $C_{3-6}$ cycloalkyl; and (ii) a cationic monomer conforming to Formula CM:

Formula CM

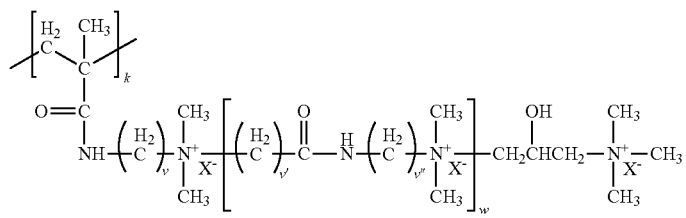

where k=1, each of v, v', and v" is independently an integer of from 1 to 6, w is zero or an integer of from 1 to 10, and $X^-$ is an anion.

In an embodiment, cationic monomer conforming to Formula CM and where k=1, v=3 and w=0, z=1 and $X^-$ is $Cl^-$ to form the following structure:

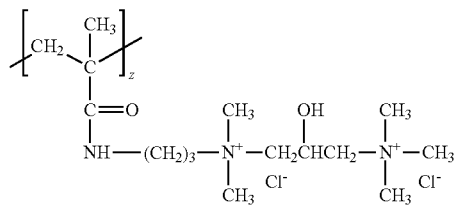

The above structure may be referred to as diquat. In another embodiment, the cationic monomer conforms to Formula CM and wherein v and v" are each 3, v'=1, w=1, y=1 and $X^-$ is $Cl^-$, such as:

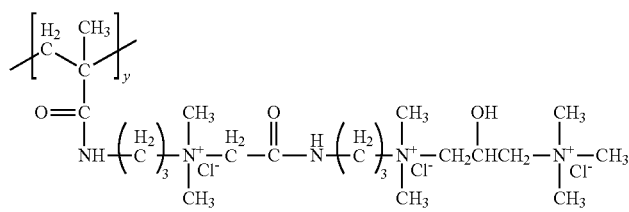

The above structure may be referred to as triquat.

In an embodiment, the acrylamide monomer is either acrylamide or methacrylamide.

In an embodiment, the cationic copolymer (b) is AM:TRIQUAT which is a copolymer of acrylamide and 1,3-Propanediaminium,N-[2-[[[dimethyl[3-[(2-methyl-1-oxo-2-propenyl)amino]propyl]ammonio]acetyl]amino]ethyl]2-hydroxy-N,N,N',N',N'-pentamethyl-, trichloride. AM:TRIQUAT is also known as polyquaternium 76 (PQ76). AM:TRIQUAT may have a charge density of 1.6 meq/g and a M.Wt. of 1.1 million g/mol.

In an alternative embodiment, the cationic copolymer is of an acrylamide monomer and a cationic monomer, wherein the cationic monomer is selected from the group consisting of: dimethylaminoethyl (meth)acrylate, dimethylaminopropyl (meth)acrylate, ditertiobutylaminoethyl (meth)acrylate, dimethylaminomethyl (meth)acrylamide, dimethylaminopropyl (meth)acrylamide; ethylenimine, vinylamine, 2-vinylpyridine, 4-vinylpyridine; trimethylammonium ethyl (meth)acrylate chloride, trimethylammonium ethyl (meth)acrylate methyl sulphate, dimethylammonium ethyl (meth)acrylate benzyl chloride, 4-benzoylbenzyl dimethylammonium ethyl acrylate chloride, trimethyl ammonium ethyl (meth)acrylamido chloride, trimethyl ammonium propyl (meth)acrylamido chloride, vinylbenzyl trimethyl ammonium chloride, diallyldimethyl ammonium chloride, and mixtures thereof.

In an embodiment, the cationic copolymer comprises a cationic monomer selected from the group consisting of: cationic monomers include trimethylammonium ethyl (meth) acrylate chloride, trimethylammonium ethyl (meth)acrylate methyl sulphate, dimethylammonium ethyl (meth)acrylate benzyl chloride, 4-benzoylbenzyl dimethylammonium ethyl acrylate chloride, trimethyl ammonium ethyl (meth)acrylamido chloride, trimethyl ammonium propyl (meth)acrylamido chloride, vinylbenzyl trimethyl ammonium chloride, and mixtures thereof.

In an embodiment, the cationic copolymer is water-soluble. In an embodiment, the cationic copolymer is formed from (1) copolymers of (meth)acrylamide and cationic monomers based on (meth)acrylamide, and/or hydrolysis-stable cationic monomers, (2) terpolymers of (meth)acrylamide, monomers based on cationic (meth)acrylic acid esters, and monomers based on (meth)acrylamide, and/or hydrolysis-stable cationic monomers. Monomers based on cationic (meth)acrylic acid esters may be cationized esters of the (meth)acrylic acid containing a quaternized N atom. In an embodiment, cationized esters of the (meth)acrylic acid containing a quaternized N atom are quaternized dialkylaminoalkyl (meth)acrylates with C1 to C3 in the alkyl and alkylene groups. In an embodiment, the cationized esters of the (meth)acrylic acid containing a quaternized N atom are selected from the group consisting of: ammonium salts of dimethylaminomethyl (meth)acrylate, dimethylaminoethyl (meth)acrylate, dimethylaminopropyl (meth)acrylate, diethylaminomethyl (meth)acrylate, diethylaminoethyl (meth)acrylate; and diethylaminopropyl (meth)acrylate quaternized with methyl chloride. In an embodiment, the cationized esters of the (meth)acrylic acid containing a quaternized N atom is dimethylaminoethyl acrylate, which is quaternized with an alkyl halide, or with methyl chloride or benzyl chloride or dimethyl sulfate (ADAME-Quat). In an embodiment, the cationic monomer when based on (meth)acrylamides are quaternized dialkylaminoalkyl(meth)acrylamides with C1 to C3 in the alkyl and alkylene groups, or dimethylaminopropylacrylamide, which is quaternized with an alkyl halide, or methyl chloride or benzyl chloride or dimethyl sulfate.

In an embodiment, the cationic monomer based on a (meth)acrylamide is a quaternized dialkylaminoalkyl(meth)acrylamide with C1 to C3 in the alkyl and alkylene groups. In an embodiment, the cationic monomer based on a (meth)acrylamide is dimethylaminopropylacrylamide, which is quaternized with an alkyl halide, especially methyl chloride or benzyl chloride or dimethyl sulfate.

In an embodiment, the cationic monomer is a hydrolysis-stable cationic monomer. Hydrolysis-stable cationic monomers can be, in addition to a dialkylaminoalkyl(meth)acrylamide, all monomers that can be regarded as stable to the OECD hydrolysis test. In an embodiment, the cationic monomer is hydrolysis-stable and the hydrolysis-stable cationic monomer is selected from the group consisting of: diallyldimethylammonium chloride and water-soluble, cationic styrene derivatives.

In an embodiment, the cationic copolymer is a terpolymer of acrylamide, 2-dimethylammoniumethyl (meth)acrylate quaternized with methyl chloride (ADAME-Q) and 3-dimethylammoniumpropyl(meth)acrylamide quaternized with methyl chloride (DIMAPA-Q). In an embodiment, the cationic copolymer is formed from acrylamide and acrylamidopropyltrimethylammonium chloride, wherein the acrylamidopropyltrimethylammonium chloride has a charge density of from about 1.0 meq/g to about 3.0 meq/g.

In an embodiment, the cationic copolymer has a charge density of from about 1.1 meq/g to about 2.5 meq/g, or from about 1.1 meq/g to about 2.3 meq/g, or from about 1.2 meq/g to about 2.2 meq/g, or from about 1.2 meq/g to about 2.1 meq/g, or from about 1.3 meq/g to about 2.0 meq/g, or from about 1.3 meq/g to about 1.9 meq/g.

In an embodiment, the cationic copolymer has a M.Wt. from about 100 thousand g/mol to about 2 million g/mol, or from about 300 thousand g/mol to about 1.8 million g/mol, or from about 500 thousand g/mol to about 1.6 million g/mol, or from about 700 thousand g/mol to about 1.4 million g/mol, or from about 900 thousand g/mol to about 1.2 million g/mol.

In an embodiment, the cationic copolymer is a trimethylammoniopropylmethacrylamide chloride-N-Acrylamide copolymer, which is also known as AM:MAPTAC. AM:MAPTAC may have a charge density of about 1.3 meq/g and a M.Wt. of about 1.1 million g/mol. In an embodiment, the cationic copolymer is AM:ATPAC. AM:ATPAC may have a charge density of about 1.8 meq/g and a M.Wt. of about 1.1 million g/mol.

In an embodiment, the cationic guar polymer (a) and the cationic copolymer (b) are present in the composition. In another embodiment, the cationic guar polymer and the cationic copolymer are added to the composition as a blend. Such a blend is disclosed in US2011/0002868A1 (Bierganns et al, filed Jul. 1, 2010), which is incorporated herein by reference. In particular, referring to the published text of US2011/0002868A1, paragraphs 0042 to 0047 describe cationic copolymers and paragraphs 0092 to 0095 describe inter alia cationic guar polymers. In an embodiment, the blend comprises the cationic guar polymer (a) and the cationic copolymer (b), wherein the cationic copolymer is AM:APTAC. For example, blends of cationic guar and AM:APTAC that are within the scope of this invention are available from Ashland. For example, a blend from Ashland is available, which is a blend of 95:5 guar hydroxypropyltrimonium chloride (M.Wt. 500,000 g/mol; charge density 1.1 meq/g) to AM/APTAC (M.Wt. 1.1 million g/mol; charge density 1.8 meq/g) i.e. a ratio of 19:1 cationic guar polymer (a) to the cationic copolymer (b).

The blend may comprise a cationic copolymer, wherein the cationic copolymer is formed from (1) copolymers of (meth)acrylamide and cationic monomers based on (meth)acrylamide, and/or hydrolysis-stable cationic monomers, (2) terpolymers of (meth)acrylamide, monomers based on cationic (meth)acrylic acid esters, and monomers based on (meth)acrylamide, and/or hydrolysis-stable cationic monomers. In an embodiment, the blend is a combination of a cationic, water-soluble, synthetic copolymer and a polygalactomannan or a polyglucomannan, wherein the polygalactomannan and the polyglucomannan are derived from guar and contain quaternary ammonium groups covalently attached to the polysaccharide backbone. In an embodiment, said polygalactomannan or said polyglucomannan have a cationic degree of substitution (DS) having a lower limit of about 0.03 and an upper limit of about 0.7. In an embodiment, the lower limit of the cationic DS is about 0.04, or about 0.06, or about 0.08, or about 0.1, or about 0.2. In an embodiment, the upper limit of the cationic DS is about 0.6, or about 0.5, or about 0.4, or about 0.3. In an embodiment, said polygalactomannan or said polyglucomannan have a charge density of from about 0.1 to about 2.5 meq/g.

According to an embodiment, the weight sum of cationic guar polyer (a)+the cationic copolymer (b) is an amount of from about 0.0001% to less than about 0.6%, by total weight of the composition. The sum of (a)+(b) means the total weight percentage of cationic guar polymer as defined herein and cationic copolymer as defined herein, by total weight of the composition. In an embodiment, the sum of (a)+(b) is from about 0.01% to less than about 0.6%, or from about 0.1% less than about 0.5%, or from about 0.1% less than about 0.4%, or from about 0.2% less than about 0.3%, by total weight of the composition. The sum of (a)+(b) is at the amount defined herein because above this level, the coacervate floc size starts to become too large for achieving good benefit. Larger floc size results in more coacervate particles being trapped between hair fibres, and therefore do not effectively reach the scalp, i.e., lower on-scalp deposition, and hence cannot so effectively deliver the benefit.

According to one embodiment, the weight ratio of (a):(b) is from about 1000:1 to about 2:1. In an embodiment, the weight ratio of (a):(b) is from about 1000:1 to about 4:1. In an embodiment, weight ratio of (a):(b) is from about 800:1 to about 4:1, or from about 500:1 to about 4:1, or from about 100:1 to about 5:1, or from about 100:1 to about 6:1, or from about 50:1 to about 6.5:1, or from about 50:1 to about 7:1, or from about 50:1 to about 8.3:1, or from about 50:1 to about 16.7:1.

C. Anionic Surfactant

According to embodiments of the present invention, the composition comprises an anionic surfactant. The anionic surfactant is included to provide cleaning performance to the composition. The anionic surfactant should be physically and chemically compatible with the essential components described herein, or should not otherwise unduly impair product stability, aesthetics, or performance. In an embodiment, the personal care composition further includes a co-surfactant, such as amphoteric surfactants, zwitterionic surfactants, cationic surfactants, non-ionic surfactants, and mixtures thereof. In an embodiment, the composition comprises from about 5% to about 50%, or from about 8% to about 30%, or from about 10% to about 25% of a surfactant, by total weight of the composition.

The composition may comprise a detersive surfactant system. The detersive surfactant system may comprise at least one anionic surfactant, and optionally a co-surfactant selected from the group consisting of: an amphoteric surfactant, a zwitterionic surfactant, a cationic surfactant, a nonionic surfactant, or a mixture thereof. The concentration of the detersive surfactant system in the composition should be sufficient to provide the desired cleaning and lather performance. In an embodiment, the composition comprises from about 5% to about 50%, or from about 8% to about 30%, or from about 10% to about 25% of detersive surfactant system, by total weight of the composition.

In considering the performance characteristics, such as coacervate formation, wet conditioning performance, dry conditioning performance, and conditioning agent deposition on hair, it is desirable to optimize the levels and types of surfactants in order to maximize the performance potential of polymer systems. In one embodiment, the detersive surfactant system for use in the composition comprises an anionic surfactant with an ethoxylate level and an anion level, wherein the ethoxylate level is from about 1 to about 10, and wherein the anion level is from about 1 to about 10. The combination of such an anionic surfactant with the cationic copolymer and cationic guar polymer provides enhanced deposition of conditioning agents to hair and/or skin without reducing cleansing or lathering performance. An optimal ethoxylate level is calculated based on the stoichiometry of the surfactant structure, which in turn is based on a particular M.Wt. of the surfactant where the number of moles of ethoxylation is known. Likewise, given a specific M.Wt. of a surfactant and an anionization reaction completion measurement, the anion level can be calculated.

In an embodiment, the detersive surfactant system comprises at least one anionic surfactant comprising an anion selected from the group consisting of sulfates, sulfonates, sulfosuccinates, isethionates, carboxylates, phosphates, and phosphonates. In an embodiment, the anion is a sulfate.

In an embodiment, the anionic surfactant is an alkyl sulfate or an alkyl ether sulfate. These materials have the respective formulae $R^9OSO_3M$ and $R^9O(C_2H_4O)_mSO_3M$, wherein $R^9$ is alkyl or alkenyl of from about 8 to about 18 carbon atoms, 'm' is an integer having a value of from about 1 to about 10, and M is a cation such as ammonium, a monovalent metal cation such as sodium and potassium, or a polyvalent metal cation such as magnesium and calcium. Solubility of the surfactant will depend upon the particular anionic surfactants and cations chosen. In one embodiment, $R^9$ has from about 8 to about 18 carbon atoms, or from about 10 to about 16 carbon atoms, or from about 12 to about 14 carbon atoms, in both the alkyl sulfates and alkyl ether sulfates. The alkyl ether sulfates are typically made as condensation products of ethylene oxide and monohydric alcohols having from about 8 to about 24 carbon atoms. The alcohols can be synthetic or they can be derived from fats, e.g., coconut oil, palm kernel oil, tallow. In an embodiment, the alcohols are lauryl alcohol and straight chain alcohols derived from coconut oil or palm kernel oil. Such alcohols are reacted with from about 0 to about 10, or from about 2 to about 5, or about 3, molar proportions of ethylene oxide, and the resulting mixture of molecular species having, for example, an average of 3 moles of ethylene oxide per mole of alcohol is sulfated and neutralized. In an embodiment, the alkyl ether sulphate is selected from the group consisting of: sodium and ammonium salts of coconut alkyl triethylene glycol ether sulfate, tallow alkyl triethylene glycol ether sulfate, tallow alkyl hexa-oxyethylene sulphate, and mixtures thereof. In an embodiment, the alkyl ether sulfate comprises a mixture of individual compounds, wherein the compounds in the mixture have an average alkyl chain length of from about 10 to about 16 carbon atoms and an average degree of ethoxylation of from about 1 to about 4 moles of ethylene oxide. Such a mixture also comprises from about 0% to about 20% $C_{12-13}$ compounds; from about 60% to about 100% of $C_{14-15-16}$ compounds; from about 0% to about 20% by weight of $C_{17-18-19}$ compounds; from about 3% to about 30% by weight of compounds having a degree of ethoxylation of 0; from about 45% to about 90% by weight of compounds having a degree of ethoxylation from about 1 to about 4; from about 10% to about 25% by weight of compounds having a degree of ethoxylation from about 4 to about 8; and from about 0.1% to about 15% by weight of compounds having a degree of ethoxylation greater than about 8.

In an embodiment, the anionic surfactant is selected from the group consisting of: ammonium lauryl sulfate, ammonium laureth sulfate, triethylamine lauryl sulfate, triethylamine laureth sulfate, triethanolamine lauryl sulfate, triethanolamine laureth sulfate, monoethanolamine lauryl sulfate, monoethanolamine laureth sulfate, diethanolamine lauryl sulfate, diethanolamine laureth sulfate, lauric monoglyceride sodium sulfate, sodium lauryl sulfate, sodium laureth sulfate, potassium lauryl sulfate, potassium laureth sulfate, sodium lauryl sarcosinate, sodium lauroyl sarcosinate, lauryl sarcosine, cocoyl sarcosine, ammonium cocoyl sulfate, ammonium lauroyl sulfate, sodium cocoyl sulfate, sodium lauroyl sulfate, potassium cocoyl sulfate, potassium lauryl sulfate, triethanolamine lauryl sulfate, triethanolamine lauryl sulfate, monoethanolamine cocoyl sulfate, monoethanolamine lauryl sulfate, and mixtures thereof. In addition to the sulfates, isethionates, sulfonates, sulfosuccinates described above, other potential anions for the anionic surfactant include phosphonates, phosphates, and carboxylates. The composition and/or the detersive surfactant system may comprise a co-surfactant selected from the group consisting of: amphoteric surfactants, zwitterionic surfactants, cationic surfactants, non-ionic surfactants, and mixtures thereof. The concentration of such co-surfactants may be from about 0.5% to about 20%, or from about 1% to about 10%, by total weight of the composition. In an embodiment, the composition comprises a co-surfactant selected from the group consisting of: amphoteric surfactants, zwitterionic surfactants, and mixtures thereof. Non limiting examples of suitable zwitterionic or amphoteric surfactants are described in U.S. Pat. No. 5,104,646 (Bolich Jr. et al.), U.S. Pat. No. 5,106,609 (Bolich Jr. et al.).

Amphoteric surfactants suitable for use in the composition are well known in the art, and include those surfactants broadly described as derivatives of aliphatic secondary and tertiary amines in which the aliphatic radical can be straight or branched chain and wherein one of the aliphatic substituents contains from about 8 to about 18 carbon atoms and one contains an anionic group such as carboxy, sulfonate, sulfate, phosphate, or phosphonate. In an embodiment, the amphoteric surfactant is selected from the group consisting of: sodium cocaminopropionate, sodium cocaminodipropionate, sodium cocoamphoacetate, sodium cocoamphohydroxypropylsulfonate, sodium cocoamphopropionate, sodium cornamphopropionate, sodium lauraminopropionate, sodium lauroamphoacetate, sodium lauroamphohydroxypropylsulfonate, sodium lauroamphopropionate, sodium cornamphopropionate, sodium lauriminodipropionate, ammonium cocaminopropionate, ammonium cocaminodipropionate, ammonium cocoamphoacetate, ammonium cocoamphohydroxypropylsulfonate, ammonium cocoamphopropionate, ammonium cornamphopropionate, ammonium lauraminopropionate, ammonium lauroamphoacetate, ammonium lauroamphohydroxypropylsulfonate, ammonium lauroamphopropionate, ammonium cornamphopropionate, ammonium lauriminodipropionate, triethanonlamine cocaminopropionate, triethanonlamine cocaminodipropionate, triethanonlamine cocoamphoacetate, triethanonlamine cocoamphohydroxypropylsulfonate, triethanonlamine cocoamphopropionate, triethanonlamine cornamphopropionate, triethanonlamine lauraminopropionate, triethanonlamine lauroamphoacetate, triethanonlamine lauroamphohydroxypropylsulfonate, triethanonlamine lauroamphopropionate, triethanonlamine cornamphopropionate, triethanonlamine lauriminodipropionate, cocoamphodipropionic acid, disodium caproamphodiacetate, disodium caproamphoadipropionate, disodium capryloamphodiacetate, disodium capryloamphodipriopionate, disodium cocoamphocarboxyethylhydroxypropylsulfonate, disodium cocoamphodiacetate, disodium cocoamphodipropionate, disodium dicarboxyethylcocopropylenediamine, disodium laureth-5 carboxyamphodiacetate, disodium lauriminodipropionate, disodium lauroamphodiacetate, disodium lauroamphodipropionate, disodium oleoamphodipropionate, disodium PPG-2-isodecethy-7 carboxyamphodiacetate, lauraminopropionic acid, lauroamphodipropionic acid, lauryl aminopropylglycine, lauryl diethylenediaminoglycine, and mixtures thereof.

In one embodiment, the amphoteric surfactant is a surfactant according to the following structure:

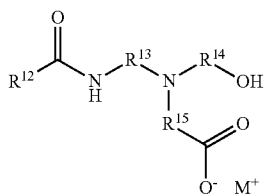

wherein $R^{12}$ is a C-linked monovalent substituent selected from the group consisting of substituted alkyl systems comprising 9 to 15 carbon atoms, unsubstituted alkyl systems comprising 9 to 15 carbon atoms, straight alkyl systems comprising 9 to 15 carbon atoms, branched alkyl systems comprising 9 to 15 carbon atoms, and unsaturated alkyl systems comprising 9 to 15 carbon atoms; $R^{13}$, $R^{14}$, and $R^{15}$ are each independently selected from the group consisting of C-linked divalent straight alkyl systems comprising 1 to 3 carbon atoms, and C-linked divalent branched alkyl systems comprising 1 to 3 carbon atoms; and $M^+$ is a monovalent counterion selected from the group consisting of sodium, ammonium and protonated triethanolamine. In an embodiment, the amphoteric surfactant is selected from the group consisting of: sodium cocoamphoacetate, sodium cocoamphodiacetate, sodium lauroamphoacetate, sodium lauroamphodiacetate, ammonium lauroamphoacetate, ammonium cocoamphoacetate, triethanolamine lauroamphoacetate, triethanolamine cocoamphoacetate, and mixtures thereof.

In one embodiment, the composition comprises a zwitterionic surfactant, wherein the zwitterionic surfactant is a derivative is a derivatives of aliphatic quaternary ammonium, phosphonium, and sulfonium compounds, in which the aliphatic radicals can be straight or branched chain, and wherein one of the aliphatic substituents contains from about 8 to about 18 carbon atoms and one contains an anionic group such as carboxy, sulfonate, sulfate, phosphate or phosphonate. In an embodiment, the zwitterionic surfactant is selected from the group consisting of: cocamidoethyl betaine, cocamidopropylamine oxide, cocamidopropyl betaine, cocamidopropyl dimethylaminohydroxypropyl hydrolyzed collagen, cocamidopropyldimonium hydroxypropyl hydrolyzed collagen, cocamidopropyl hydroxysultaine, cocobetaineamido amphopropionate, coco-betaine, coco-hydroxysultaine, coco/oleamidopropyl betaine, coco-sultaine, lauramidopropyl betaine, lauryl betaine, lauryl hydroxysultaine, lauryl sultaine, and mixtures thereof. In an embodiment, the zwitterionic surfactant is lauryl hydroxysultaine. In an embodiment, the zwitterionic surfactant is selected from the group consisting of: lauryl hydroxysultaine, cocamidopropyl hydroxysultaine, coco-betaine, coco-hydroxysultaine, cocosultaine, lauryl betaine, lauryl sultaine, and mixtures thereof.

In an embodiment, the co-surfactant is selected from the group consisting of: zwitterionic surfactants, amphoteric surfactants, non-ionic surfactants, and mixtures thereof. In an embodiment, the surfactant is an anionic surfactant and the composition further comprises a co-surfactant, wherein the co-surfactant is selected from the group consisting of: zwitterionic surfactants, amphoteric surfactants, non-ionic surfactants, and mixtures thereof. In an embodiment, the co-surfactant is a non-ionic surfactant selected from the group consisting of: Cocamide, Cocamide Methyl MEA, Cocamide DEA, Cocamide MEA, Cocamide MIPA, Lauramide DEA, Lauramide MEA, Lauramide MIPA, Myristamide DEA, Myristamide MEA, PEG-20 Cocamide MEA, PEG-2 Cocamide, PEG-3 Cocamide, PEG-4 Cocamide, PEG-5 Cocamide, PEG-6 Cocamide, PEG-7 Cocamide, PEG-3 Lauramide, PEG-5 Lauramide, PEG-3 Oleamide, PPG-2 Cocamide, PPG-2 Hydroxyethyl Cocamide, and mixtures thereof. In an embodiment, the co-surfactant is a zwitterionic surfactant, wherein the zwitterionic surfactant is selected from the group consisting of: lauryl hydroxysultaine, cocamidopropyl hydroxysultaine, coco-betaine, coco-hydroxysultaine, cocosultaine, lauryl betaine, lauryl sultaine, and mixtures thereof.

In an embodiment, the composition comprises a non-ionic surfactant, wherein the surfactant is an anionic surfactant and the composition further comprises a co-surfactant D. Carrier In accordance with another embodiment, the composition further comprises a cosmetically acceptable carrier. In an embodiment, the carrier is an aqueous carrier. The amount and chemistry of the carrier is selected according to the compatibility with other components and other desired characteristic of the product. In an embodiment, the carrier is selected from the group consisting of: water and water solutions of lower alkyl alcohols. Lower alkyl alcohols useful herein are monohydric alcohols having 1 to 6 carbons, such as ethanol and/or isopropanol. In an embodiment, the cosmetically acceptable carrier is a cosmetically acceptable aqueous carrier and is present at a level of from about 20% to about 95%, or from about 60% to about 85%.

The pH composition may be from about pH 3 to about pH 9, or from about pH 4 to about pH 7.

E. Benefit Agent

In accordance with embodiments of the present invention, the personal care composition may further comprise one or more benefit agents. Exemplary benefit agents include, but are not limited to, particles, colorants, anti-dandruff actives, perfume microcapsules, gel networks, and other insoluble skin or hair conditioning agents such as skin silicones, natural oils such as sun flower oil or castor oil.

In accordance with another embodiment, the composition may further comprise an anti-dandruff active, which may be an anti-dandruff active particulate. In an embodiment, the anti-dandruff active is selected from the group consisting of: pyridinethione salts; zinc carbonate; azoles, such as ketoconazole, econazole, and elubiol; selenium sulphide; particulate sulfur; keratolytic agents such as salicylic acid; and mixtures thereof. In an embodiment, the anti-dandruff particulate is a pyridinethione salt. Such anti-dandruff particulate should be physically and chemically compatible with the components of the composition, and should not otherwise unduly impair product stability, aesthetics, or performance.

Pyridinethione particulates are suitable particulate anti-dandruff actives for use in composition of the present invention. In an embodiment, the anti-dandruff active is a 1-hydroxy-2-pyridinethione salt and is in particulate form. In an embodiment, the concentration of pyridinethione anti-dandruff particulate ranges from about 0.01% to about 5%, by weight of the composition, or from about 0.1% to about 3%, or from about 0.1% to about 2%. In an embodiment, the pyridinethione salts are those formed from heavy metals such as zinc, tin, cadmium, magnesium, aluminium and zirconium, generally zinc, typically the zinc salt of 1-hydroxy-2-pyridinethione (known as "zinc pyridinethione" or "ZPT"), commonly 1-hydroxy-2-pyridinethione salts in platelet particle form. In an embodiment, the 1-hydroxy-2-pyridinethione salts in platelet particle form have an average particle size of up to about 20 microns, or up to about 5 microns, or up to about 2.5 microns. Salts formed from other cations, such as sodium, may also be suitable. Pyridinethione anti-dandruff actives are described, for example, in U.S. Pat. Nos. 2,809,971; 3,236,733; 3,753,196; 3,761,418; 4,345,080; 4,323,683; 4,379,753; and 4,470,982.

In an embodiment, in addition to the anti-dandruff active selected from polyvalent metal salts of pyrithione, the composition further comprises one or more anti-fungal and/or anti-microbial actives. In an embodiment, the anti-microbial active is selected from the group consisting of: coal tar, sulfur, charcoal, whitfield's ointment, castellani's paint, aluminum chloride, gentian violet, octopirox (piroctone olamine), ciclopirox olamine, undecylenic acid and its metal salts, potassium permanganate, selenium sulphide, sodium thiosulfate, propylene glycol, oil of bitter orange, urea preparations, griseofulvin, 8-hydroxyquinoline ciloquinol, thiobendazole, thiocarbamates, haloprogin, polyenes, hydroxypyridone, morpholine, benzylamine, allylamines (such as terbinafine), tea tree oil, clove leaf oil, coriander, palmarosa, berberine, thyme red, cinnamon oil, cinnamic aldehyde, citronellic acid, hinokitol, ichthyol pale, Sensiva SC-50, Elestab HP-100, azelaic acid, lyticase, iodopropynyl butylcarbamate (IPBC), isothiazalinones such as octyl isothiazalinone, and azoles, and mixtures thereof. In an embodiment, the anti-microbial is selected from the group consisting of: itraconazole, ketoconazole, selenium sulphide, coal tar, and mixtures thereof.

In an embodiment, the azole anti-microbials is an imidazole selected from the group consisting of: benzimidazole, benzothiazole, bifonazole, butaconazole nitrate, climbazole, clotrimazole, croconazole, eberconazole, econazole, elubiol, fenticonazole, fluconazole, flutimazole, isoconazole, ketoconazole, lanoconazole, metronidazole, miconazole, neticonazole, omoconazole, oxiconazole nitrate, sertaconazole, sulconazole nitrate, tioconazole, thiazole, and mixtures thereof, or the azole anti-microbials is a triazole selected from the group consisting of: terconazole, itraconazole, and mixtures thereof. When present in the composition, the azole anti-microbial active is included in an amount of from about 0.01% to about 5%, or from about 0.1% to about 3%, or from about 0.3% to about 2%, by total weight of the composition. In an embodiment, the azole anti-microbial active is ketoconazole. In an embodiment, the sole anti-microbial active is ketoconazole.

The present invention may also comprise a combination of anti-microbial actives. In an embodiment, the combination of anti-microbial active is selected from the group of combinations consisting of: octopirox and zinc pyrithione, pine tar and sulfur, salicylic acid and zinc pyrithione, salicylic acid and elubiol, zinc pyrithione and elubiol, zinc pyrithione and climbasole, octopirox and climbasole, salicylic acid and octopirox, and mixtures thereof.

In an embodiment, the composition comprises an effective amount of a zinc-containing layered material. In an embodiment, the composition comprises from about 0.001% to about 10%, or from about 0.01% to about 7%, or from about 0.1% to about 5% of a zinc-containing layered material, by total weight of the composition.

Zinc-containing layered materials may be those with crystal growth primarily occurring in two dimensions. It is conventional to describe layer structures as not only those in which all the atoms are incorporated in well-defined layers, but also those in which there are ions or molecules between the layers, called gallery ions (A. F. Wells "Structural Inorganic Chemistry" Clarendon Press, 1975) Zinc-containing layered materials (ZLMs) may have zinc incorporated in the layers and/or be components of the gallery ions. The following classes of ZLMs represent relatively common examples of the general category and are not intended to be limiting as to the broader scope of materials which fit this definition.

Many ZLMs occur naturally as minerals. In an embodiment, the ZLM is selected from the group consisting of: hydrozincite (zinc carbonate hydroxide), basic zinc carbonate, aurichalcite (zinc copper carbonate hydroxide), rosasite (copper zinc carbonate hydroxide), and mixtures thereof. Related minerals that are zinc-containing may also be included in the composition. Natural ZLMs can also occur wherein anionic layer species such as clay-type minerals (e.g., phyllosilicates) contain ion-exchanged zinc gallery ions. All of these natural materials can also be obtained synthetically or formed in situ in a composition or during a production process.

Another common class of ZLMs, which are often, but not always, synthetic, is layered double hydroxides. In an embodiment, the ZLM is a layered double hydroxide conforming to the formula $[M^{2+}_{1+x}M^{3+}_{x}(OH)_2]^{x+}A^{m-}_{x/m} \cdot nH_2O$ wherein some or all of the divalent ions ($M^{2+}$) are zinc ions (Crepaldi, E L, Pava, P C, Tronto, J, Valim, J B *J. Colloid Interfac. Sci.* 2002, 248, 429-42).

Yet another class of ZLMs can be prepared called hydroxy double salts (Morioka, H., Tagaya, H., Karasu, M, Kadokawa, J, Chiba, K *Inorg. Chem.* 1999, 38, 4211-6). In an embodiment, the ZLM is a hydroxy double salt conforming to the formula $[M^{2+}_{1+x}M^{2+}_{1+x}(OH)_{3(1-y)}]^{+}A^{n-}_{(1=3y)/n} \cdot nH_2O$ where the two metal ions ($M^{2+}$) may be the same or different. If they are the same and represented by zinc, the formula simplifies to $[Zn_{1+x}(OH)_2]^{2x+}2xA^-\cdot nH_2O$. This latter formula represents (where x=0.4) materials such as zinc hydroxychloride and zinc hydroxynitrate. In an embodiment, the ZLM is zinc hydroxychloride and/or zinc hydroxynitrate. These are related to hydrozincite as well wherein a divalent anion replace the monovalent anion. These materials can also be formed in situ in a composition or in or during a production process.

In an embodiment, the composition comprises basic zinc carbonate. Commercially available sources of basic zinc carbonate include zinc Carbonate Basic (Cater Chemicals: Bensenville, Ill., USA), zinc Carbonate (Shepherd Chemicals: Norwood, Ohio, USA), Zinc Carbonate (CPS Union Corp.: New York, N.Y., USA), zinc Carbonate (Elementis Pigments: Durham, UK), and zinc Carbonate AC (Bruggemann Chemical: Newtown Square, Pa., USA). Basic zinc carbonate, which also may be referred to commercially as "zinc Carbonate" or "zinc carbonate basic" or "zinc zydroxy carbonate", is a synthetic version consisting of materials similar to naturally occurring hydrozincite. The idealized stoichiometry is represented by $Zn_5(OH)_6(CO_3)_2$ but the actual stoichiometric ratios can vary slightly and other impurities may be incorporated in the crystal lattice.

In embodiments having a zinc-containing layered material and a pyrithione or polyvalent metal salt of pyrithione, the ratio of zinc-containing layered material to pyrithione or a polyvalent metal salt of pyrithione is from about 5:100 to about 10:1, or from about 2:10 to about 5:1, or from about 1:2 to about 3:1.

The on-scalp deposition of the anti-dandruff active is at least about 1 microgram/cm². The on-scalp deposition of the anti-dandruff active is important in view of ensuring that the anti-dandruff active reaches the scalp where it is able to perform its function. In an embodiment, the deposition of the anti-dandruff active on the scalp is at least about 1.5 microgram/cm², or at least about 2.5 microgram/cm², or at least about 3 microgram/cm², or at least about 4 microgram/cm², or at least about 6 microgram/cm², or at least about 7 microgram/cm², or at least about 8 microgram/cm², or at least about 9 microgram/cm², or at least about 10 microgram/cm². The on-scalp deposition of the anti-dandruff active is measured by having the hair of individuals washed with a composition comprising an anti-dandruff active, for example a composition pursuant to the present invention, by trained a cosmetician according to a conventional washing protocol. The hair is then parted on an area of the scalp to allow an open-ended glass cylinder to be held on the surface while an aliquot of an extraction solution is added and agitated prior to recovery and analytical determination of anti-dandruff active content by conventional methodology, such as HPLC.

F. Other Components

The personal care compositions of the present invention can also additionally comprise any suitable optional ingredients as desired. Such optional ingredients should be physically and chemically compatible with the components of the composition, and should not otherwise unduly impair product stability, aesthetics, or performance. The CTFA Cosmetic Ingredient Handbook, Tenth Edition (published by the Cosmetic, Toiletry, and Fragrance Association, Inc., Washington, D.C.) (2004) (hereinafter "CTFA"), describes a wide variety of nonlimiting materials that can be added to the composition herein.

In accordance with another embodiment of the invention, a method of making a personal care composition comprising an anionic surfactant, a cationic conditioning polymer, and a silicone emulsion is provided. The method includes (i) combining the anionic surfactant and the cationic conditioning polymer in water, and (ii) combining a silicone emulsion and an aqueous composition that includes a product of step (i) to form the personal care composition.

In an embodiment, the personal care composition has a viscosity of 4,000 cP to 20,000 cP, or from about 6,000 cP to about 12,000 cP, or from about 8,000 cP to about 11,000 cP, measured at 26.6° C. with a Brookfield R/S Plus Rheometer at $2\ s^{-1}$. cP means centipoises.

The personal care compositions in accordance with the principles of the present invention form coacervate particles upon dilution with water. The composition may be diluted such that the weight ratio of composition:water is about 1:50. According to one aspect of the coacervate, the percentage of coacervate particles with a floc size of greater than about 20 micron is from about 1% to about 60%. In an embodiment, the percentage of coacervate particles with a floc size of greater than about 20 micron is from about 1% to about 50%, or from about 1% to about 40%, or from about 1% to about 30%, or from about 2% to about 25%; or from about 5% to about 20% from about 5% to about 15%. The floc size is measured after preparing a 1:50 (w/w) dilution of the composition with water.

The floc size is measured using the Lasentec Method: In a suitable mixing vessel create a 1:9 dilution of composition in distilled water at ambient temperature and mix for 5 min at 250 rpm. Using a peristaltic pump transfer ambient distilled water into the mixing vessel at a rate of 100 g/min resulting in a final dilution of 1:50 parts composition to distilled water. After a 10 min equilibration period a Lasentec Focused Beam Reflectance Method (FBRM) [model S400A available from Mettler Toledo Corp] may be used to determine floc size and amount as measured by chord length and particle counts/sec (counts per sec).

The viscosity of the coacervate particles is measured via squeeze flow resulting in a squeeze flow viscosity. The coacervate is prepared and isolated for rheological testing as follows: A well-mixed 1:50 dilution of composition in distilled water is prepared at ambient temperature in such a quantity to produce a coacervate pellet of at least 3 grams after centrifugation at 4500 rpm for 30 min The supernatant liquid is decanted and discarded and the coacervate pellet collected. A second centrifugation step is required for 15 min at 9100 rpm to ensure sample integrity prior to measurement. Any remaining supernatant liquid is removed without disturbing the coacervate pellet collected at the bottom of the container.

In the squeeze flow experiment, the coacervate to be tested is loaded between two parallel plates of radius R on a conventional rheometer (for example, 25 mm parallel plates on a TA AR2000) equilibrated to 25° C. Sufficient coacervate is added to completely fill a gap of 1000 microns, and any excess material is trimmed prior to starting the test. The sample is allowed to relax from loading stresses for 1 min. The top plate is lowered at a constant linear velocity as the gap is decreased. During this process the normal force exerted by the sample on the lower plate is measured by the rheometer. Typical linear velocities utilized for the squeeze experiment are 10 or 100 microns/sec. The gap is decreased from 1000 microns until a final gap of 100 microns is reached or until the normal force reaches the maximum instrument tolerance.

The measured force, F, and gap, h, are further analyzed to obtain a more traditional viscosity versus shear rate format. Analysis of squeezing flow between parallel plates for Newtonian and various non-Newtonian materials has been published in the literature (*J. of Non-Newtonian Fluid Mechanics,* 132 (2005) 1-27). A power-law model is chosen to describe the coacervate since it best describes the viscosity behavior in the nonlinear region. The power-law parameters K, the power-law consistency, and n, the power-law exponent, are determined from the corresponding expression for force as a function of gap under constant area, constant linear velocity, no-slip squeeze flow (*J. of Non-Newtonian Fluid Mechanics*, 132 (2005) 1-27). The nonlinear force versus gap expression is first linearized by taking the natural log of both sides of the expression. The power-law parameters K and n are then obtained from the slope and intercept of a fit to the linear region of ln(Force) versus ln(gap) and using the known constants from the experimental conditions. Utilizing these values of K and n, the squeeze flow viscosity η can be calculated at a specific shear rate $\dot{\gamma}$ via the power-law model:

$$\eta = K \dot{\gamma}^{(n-1)}$$

This relationship is used to determine the squeeze flow viscosity at a shear rate of $100\ s^{-1}$.

The coacervate particles have a squeeze flow viscosity of from about 1 Pa·s to about 100 Pa·s, or from about 1 Pa·s to about 80 Pa·s, or from about 2 Pa·s to about 60 Pa·s, or from about 3 Pa·s to about 50 Pa·s, or from about 4 Pa·s to about 40 Pa·s, or from about 5 Pa·s to about 30 Pa·s, or from about 10 Pa·s to about 20 Pa·s, measured at 25° C. with a TA AR2000 rheometer at a $100\ s^{-1}$. Pa·s refers to Pascal seconds. The coacervate particle squeeze flow viscosity values relate to when the composition has been diluted 1 in 50 with water.

In another embodiment, a method of achieving improved hair feel is provided. The method includes applying to hair a personal care composition in accordance with the first aspect. According to one aspect of the method, a mean consumer acceptance rating, on a scale of 1 to 100, of 60 or more, or 65 or more, or 70 or more, or 75 or more, or 80 or more, or 85 or more, is achieved. In order to obtain mean consumer acceptance rating values, compositions are evaluated by consumer panels ranging in size from 10 to 400 people, for example 16 to 310 people. Panelists are asked to use the composition as their only shampoo over a period of time ranging from 3 days to 4 weeks. After use, the panelists are asked to rate different attributes of the composition and its usage experience on a 5 point scale. For the purpose of numerical analysis, the answers were converted to a 100 point scale and the mean consumer acceptance rating calculated.

According to a first aspect, a personal care composition is provided, wherein the composition comprises a) an anionic surfactant; b) a cationic conditioning polymer selected from at least one of i) a cationic guar polymer, wherein the cationic guar polymer has a weight average molecular weight of less than about 1 million g/mol, and wherein the cationic guar polymer has a charge density of from about 0.1 meq/g to about 2.5 meq/g; or ii) a cationic copolymer of an acrylamide monomer and a cationic monomer, wherein the copolymer has a charge density of from about 1.0 meq/g to about 3.0 meq/g; and c) a silicone emulsion comprising an insoluble polysiloxane having a general formula of $R^1$—[O—$SiR_2$]$_n$—$OR^{1\prime}$, wherein n is an integer, R is a substituted or unsubstituted $C_1$ to $C_{10}$ alkyl or aryl, and $R^1$ is a hydrogen or a substituted or unsubstituted $C_1$ to $C_{10}$ alkyl or aryl, wherein the insoluble polysiloxane has an average molecular weight within the range from about 50,000 to about 500,000 g/mol, and an average particle size within the range from about 30 nm to about 10 μm. The total content of a cyclic polysiloxane in the silicone emulsion is present in an amount less than about 2.5 wt % based on the total weight of the insoluble polysiloxane and the cyclic polysiloxane, wherein the cyclic polysiloxane has a general formula:

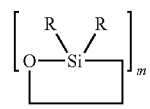

wherein R is as defined above, wherein m is 4 or 5.

According to a second aspect, a personal care composition is provided according to the first aspect, wherein the composition forms coacervate particles upon dilution with water, and wherein a percentage of the coacervate particles with a floc size of greater than about 20 micron is from about 1% to about 60% upon dilution with water at a 50:1 dilution.

According to a third aspect, a method of treating hair comprising applying to hair a composition according to the first aspect or the second aspect.

According to a fourth aspect, a method of achieving improved hair feel, comprising applying to hair a composition according to the first aspect or the second aspect.

The following examples illustrate the present invention. The exemplified compositions can be prepared by conventional formulation and mixing techniques. It will be appreciated that other modifications of the present invention within the skill of those in the hair care formulation art can be undertaken without departing from the spirit and scope of this invention. All parts, percentages, and ratios herein are by weight unless otherwise specified. Some components may come from suppliers as dilute solutions. The amount stated reflects the weight percent of the active material, unless otherwise specified.

EXAMPLES

Exemplary Personal Care Compositions Containing Insoluble Polysiloxanes

Personal care compositions in accordance with the principles of this disclosure can be prepared as set forth in Table 1.

TABLE 1

Personal care compositions

| | Component/Example | 1 | 2 | 3 | 4 | 5 | 6 | 7 | 8 |
|---|---|---|---|---|---|---|---|---|---|
| 1 | cationic guar polymer | 0.3 | 0.3 | 0.3 | 0.3 | 0.3 | — | — | — |
| 2 | cationic guar and copolymer blend | — | — | — | — | — | 0.25 | 0.4 | 0.6 |
| 3 | cationic copolymer | 0.045 | 0.045 | 0.045 | 0.045 | 0.045 | — | — | — |
| 4 | sodium laureth-3 sulfate (SLE3S) | — | — | — | — | — | — | — | — |
| 5 | sodium laureth-1 sulfate (SLE1S) | 12.5 | 12.5 | 12.5 | 12.5 | 12.5 | 10.5 | 10.5 | 10.5 |

TABLE 1-continued

Personal care compositions

| | Component/Example | 1 | 2 | 3 | 4 | 5 | 6 | 7 | 8 |
|---|---|---|---|---|---|---|---|---|---|
| 6 | sodium lauryl sulfate (SLS) | 1.5 | 1.5 | 1.5 | 1.5 | 1.5 | 1.5 | 1.5 | 1.5 |
| 7 | cocamidopropyl betaine | 1.5 | 1.5 | 1.5 | 1.5 | 1.5 | — | — | — |
| 8 | cocamide MEA | — | — | — | — | — | 1.0 | 1.0 | 1.0 |
| 9 | lauryl hydroxysultaine | — | — | — | — | — | 1.0 | 1.0 | 1.0 |
| 10 | Dimethicone | — | — | — | — | 1.0 | — | — | — |
| 11 | dimethiconol | — | 1.0 | — | 1.0 | — | 1.0 | 1.0 | 1.0 |
| 12 | Dimethiconol | — | — | 1.0 | — | — | — | — | — |
| 13 | zinc pyrithione | 1.0 | 1.0 | 1.0 | 1.0 | 1.0 | 1.0 | 1.0 | 1.0 |
| 14 | zinc carbonate | 1.61 | 1.61 | 1.61 | 1.61 | 1.61 | 1.61 | 1.61 | 1.61 |
| 15 | gel network | — | — | — | 18.18 | — | — | — | — |
| 16 | glycol distearate | 1.5 | 1.5 | 1.5 | 1.5 | 1.5 | 1.5 | 1.5 | 1.5 |
| 17 | Preservative | 0.05 | 0.05 | 0.05 | 0.05 | 0.05 | 0.05 | 0.05 | 0.05 |
| 18 | sodium benzoate | 0.25 | 0.25 | 0.25 | 0.25 | 0.25 | 0.25 | 0.25 | 0.25 |
| 19 | Fragrance | 0.75 | 0.75 | 0.75 | 0.75 | 0.75 | 0.75 | 0.75 | 0.75 |
| 20 | HCl 6N | Q.S. | Q.S. | Q.S. | Q.S. | Q.S. | Q.S. | Q.S. | Q.S. |
| 21 | sodium chloride | Q.S. | Q.S. | Q.S. | Q.S. | Q.S. | Q.S. | Q.S. | Q.S. |
| 22 | Water | Q.S. | Q.S. | Q.S. | Q.S. | Q.S. | Q.S. | Q.S. | Q.S. |

Key:
1) Jaguar C500 from Rhodia; mw 500,000 cd 0.8 meq/g
2) A blend from Ashland, which is a blend of 95:5 guar hydroxypropyltrimonium chloride (M.Wt. 500,000 g/mol; charge density 1.1 meq/g) to AM/APTAC (M.Wt. 1.1 million g/mol; charge density 1.8 meq/g).
3) PQ-76 from Rhodia; mw 1,000,000 cd 1.6 meq/g
4) Sodium laureth-3 sulfate from the Stepan Company
5) Sodium laureth-1 sulfate from the Stepan Company
6) Sodium lauryl sulfate from the Stepan Company
7) Amphosol HCA from the Stepan Company
8) Ninol COMF from the Stepan Company
9) Mackam LHS from Rhodia
10) Viscasil 330M from Momentive Performance Materials; 330,000 cSt
11) BELSIL DM from Wacker Silicones
12) DC2-1870 from Dow Corning
13) ZPT from Arch Chemical
14) Zinc carbonate from the Bruggeman Group
15) Gel Network from Procter & Gamble (see details below)
16) EGDS from Golschmidt Chemical Company
17) Kathon CG from Akzo Nobel Composition preparation: A vessel is charged with about three-quarters of the amount of deionized water. The cationic guar polymer is added to the vessel under agitation to completely disperse/hydrate the polymer. The anionic surfactant is added to the aqueous composition with controlled agitation so as to avoid excessive aeration. Under continuous agitation, pH is adjusted with HCl and the remaining components are added sequentially with optional pH adjustment therebetween. Viscosity and pH of the composition are measured and adjusted to their desired values by the addition of salt and acid, respectively.

Gel network preparation: A vessel is charged with water and the water is heated to about 74° C. Cetyl alcohol, stearyl alcohol, and SLES surfactant are added to the heated water. After incorporation, the resulting mixture is passed through a heat exchanger where the mixture is cooled to about 35° C. Upon cooling, the fatty alcohols and surfactant crystallized to form a crystalline gel network. Table 2 provides the components and their respective amounts for the gel network composition.

TABLE 2

Gel network components

| Ingredient | Wt. % |
|---|---|
| Water | 78.27% |
| Cetyl Alcohol | 4.18% |
| Steary Alcohol | 7.52% |
| Sodium laureth-3 sulfate (28% Active) | 10.00% |
| 5-Chloro-2-methyl-4-isothiazolin-3-one, Kathon CG | 0.03% |

Table 3 presents data of the effect of salt concentration on the floc size of the coacervate of exemplary compositions 2 and 3. Similarly, Table 4 presents data of the effect of salt concentration on the squeeze flow viscosity of the coacervate particles of compositions 2 and 3. And Table 5 presents data of the effect of D4/D5 concentration on the salt concentration needed to achieve target viscosity of 9,000 cps.

TABLE 3

Comparison of floc size based on salt concentration

| Percent NaCl Added | Composition 2 % flocs greater than 20 micron | Composition 3 % flocs greater than 20 micron |
|---|---|---|
| 0.0 | 2.29 | 3.03 |
| 0.1 | 2.26 | 3.00 |
| 0.2 | 2.26 | 3.38 |
| 0.3 | 2.62 | 3.65 |
| 0.4 | 2.92 | 3.90 |
| 0.5 | 4.71 | 5.03 |

TABLE 3-continued

Comparison of floc size based on salt concentration

| Percent NaCl Added | Composition 2 % flocs greater than 20 micron | Composition 3 % flocs greater than 20 micron |
|---|---|---|
| 1.0 | 8.59 | 14.46 |
| 1.5 | 16.21 | 31.35 |

As shown Table 3, increasing the salt content of the composition affects an increase in the floc size of the resultant coacervate particles, which are formed upon dilution of the composition with water (1 part composition to 50 parts water).

FIGS. 1-5 are plots of Lasentec chord length in microns (X-Axis) versus Lasentec particle counts per second (Y-Axis), where the symbols distinguish the specified weight percent of NaCl added to the composition.

FIG. 1 shows the Lasentec floc size profile for Composition 3 with no salt and subsequent 0.1% wt NaCl additions up to 0.5% wt. As shown, lower levels of NaCl (up to 0.4%) demonstrate very little effect on coacervate floc size. However, a shift to a greater concentration of larger coacervate particles is observed at 0.5% NaCl. FIG. 2 shows the Lasentec floc size profile for Composition 3 formulation with no salt and subsequent 0.5% wt NaCl additions up to 1.5% NaCl. As shown, NaCl additions greater than 0.5%, vis-à-vis the nil salt example, have a substantial impact on coacervate floc size. The shift to a greater concentration of larger coacervate flocs is observed as the NaCl concentration is increased. This salt effect on the floc size is a result of the elevated D4/D5 content of the insoluble silicone microemulsion that necessitates higher levels of salt to achieve a consumer acceptable shampoo viscosity.

Figure 3:
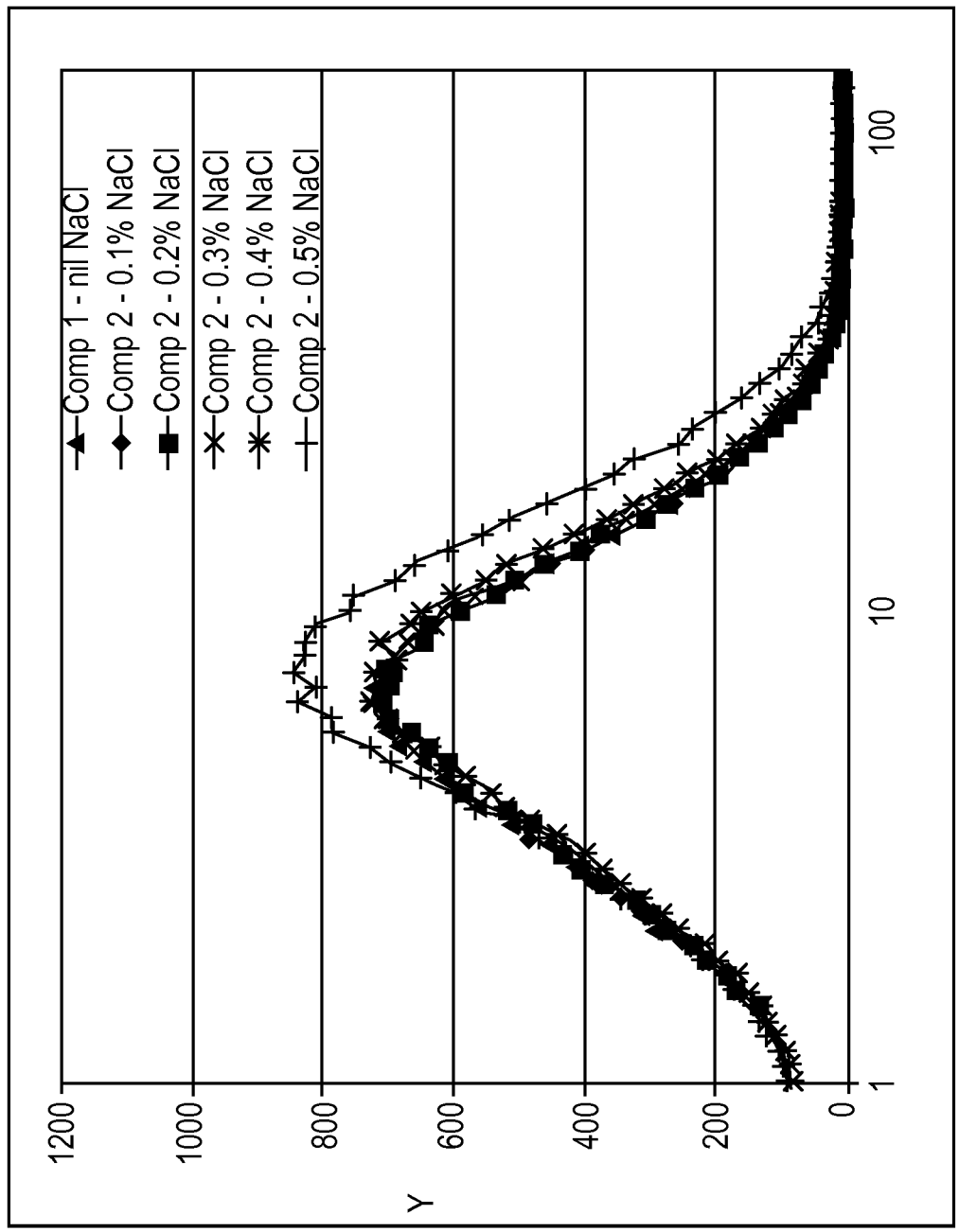
FIG. 3 is a graphical representation showing the effect of salt concentration on a floc size of a coacervate of a personal care composition in accordance with another embodiment of the present invention.
Figure 4:
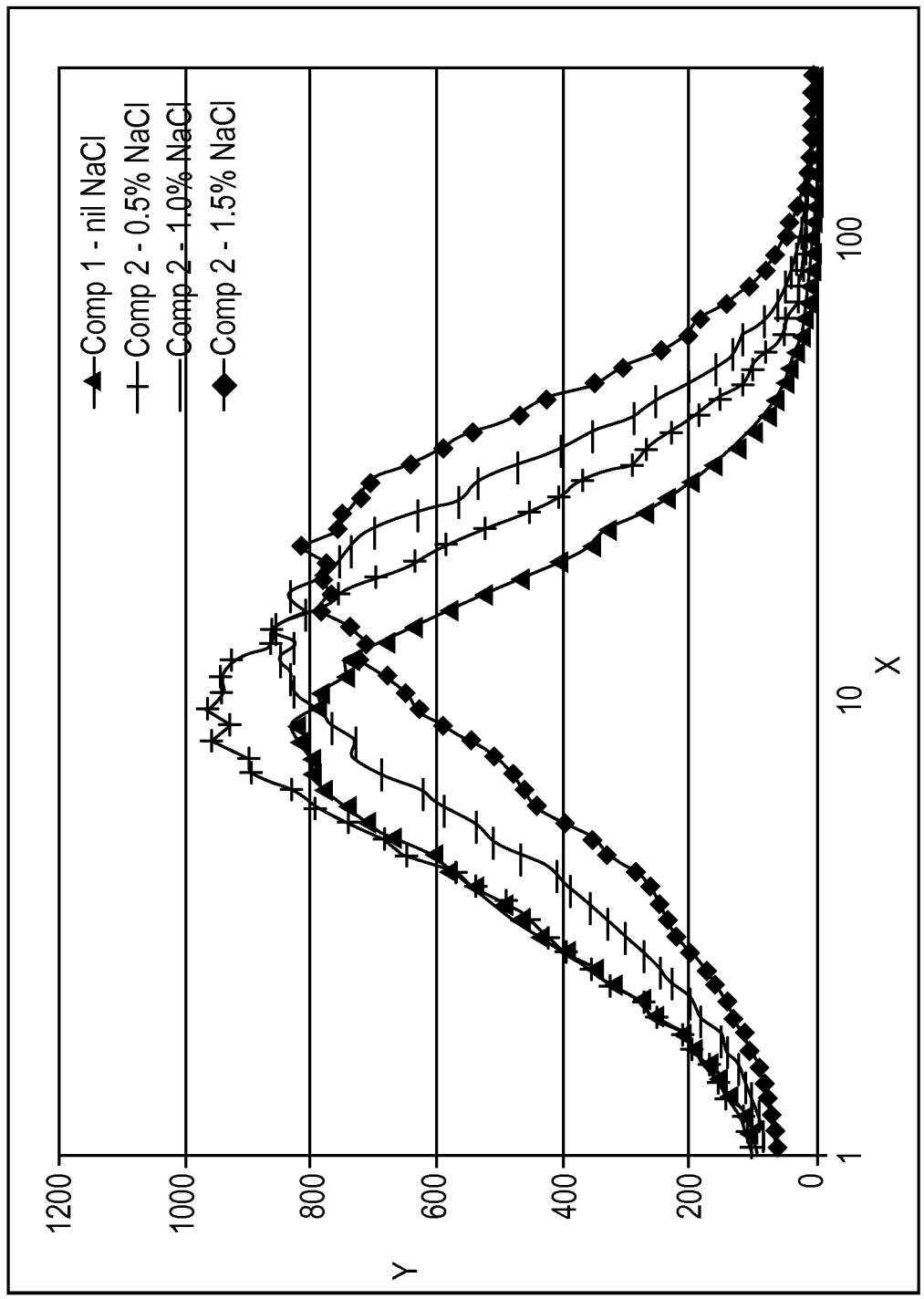
FIG. 4 is a graphical representation showing the effect of salt concentration on a floc size of a coacervate of a personal care composition in accordance with another embodiment of the present invention.

FIG. 3 shows the Lasentec floc size profile for Composition 2 with no salt and subsequent 0.1% wt NaCl additions up to 0.5% wt. As shown, lower levels of NaCl (up to 0.4%) demonstrate very little effect on coacervate floc size. However, a shift to a greater concentration of larger coacervate particles is observed at 0.5% NaCl. FIG. 4 shows the Lasentec floc size profile Composition 2 with no salt and subsequent 0.5% wt NaCl additions up to 1.5% NaCl. As shown, NaCl additions greater than 0.5% %, vis-à-vis the nil salt example, have a substantial impact on coacervate floc size. The shift to a greater concentration of larger coacervate flocs is observed as the NaCl concentration is increased.

As shown in Table 4, increasing the salt content of the composition affects an increase in the squeeze flow viscosity of the resultant coacervate particles, which are formed upon dilution of the composition with water (1 part composition to 50 parts water).

TABLE 4

Comparison of squeeze flow viscosity based on salt concentration

| Percent NaCl Added | Composition 2 coacervate viscosity at 100 s-1, Pa-s | Composition 3 coacervate viscosity at 100 s-1, Pa-s |
|---|---|---|
| 0.0 | 40.47 | 40.47 |
| 0.1 | 42.44 | 85.19 |
| 0.2 | 40.03 | 49.28 |
| 0.3 | 33.19 | 56.90 |
| 0.4 | 30.29 | 75.98 |
| 0.5 | 24.06 | 45.70 |
| 1.0 | 39.15 | 61.01 |
| 1.5 | 35.72 | 50.30 |

Figure 5:
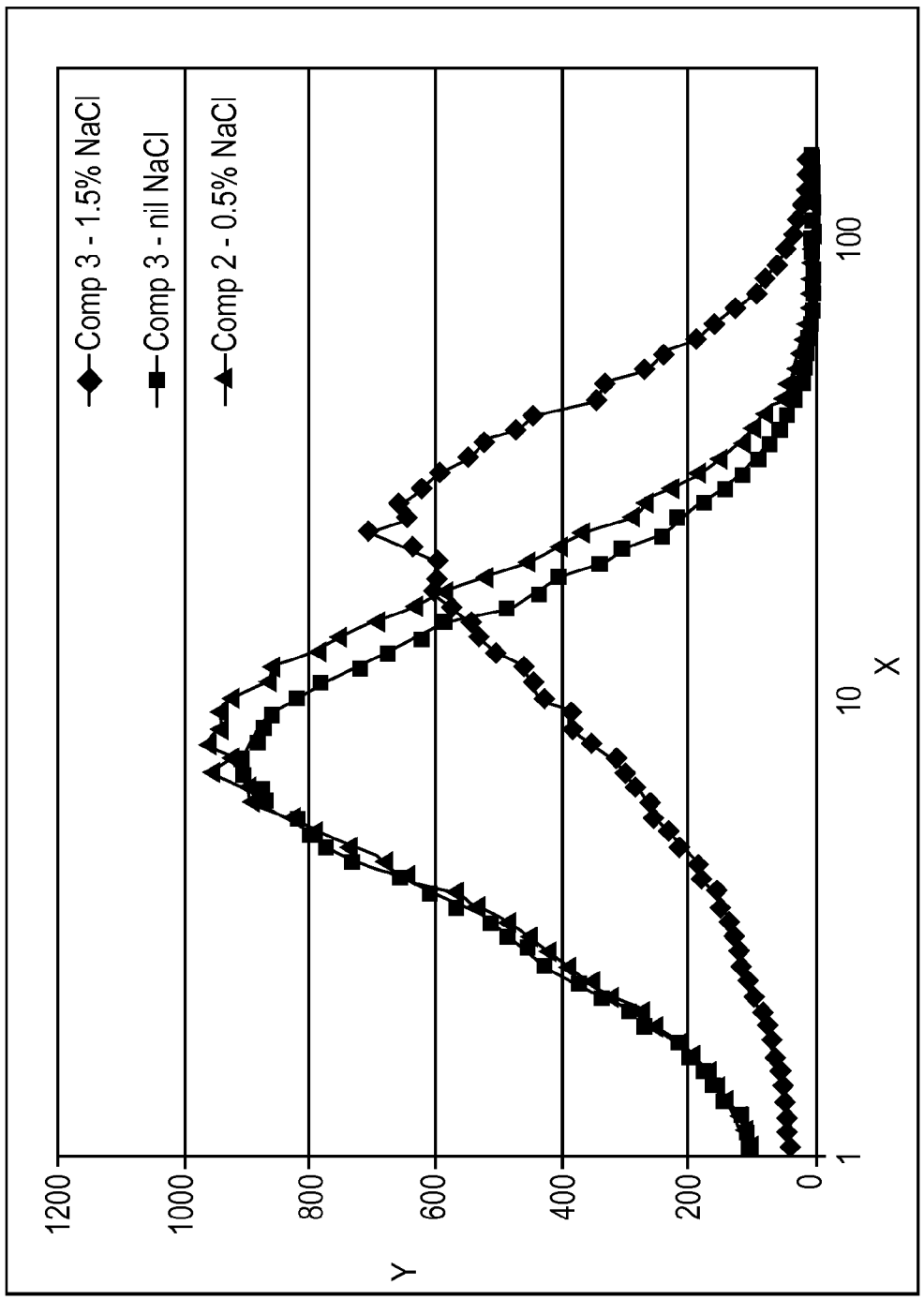
FIG. 5 is a graphical representation showing the effect of salt concentration on a floc size of a coacervate of a personal care composition in accordance with another embodiment of the present invention.

As shown in Table 5, the limiting the levels of D4 and D5 lowers the amount of salt needed to achieve a target viscosity of 9,000 cPs for the composition. As shown by a comparison of FIGS. 1 and 3, at low NaCl concentrations (<0.5% wt) floc size is similar between higher and lower D4/D5 containing compositions. However, as shown in FIG. 5, at a consumer preferred compositional viscosity of 9,000 cP at 2 s-1, a significant increase in floc size is observed in Composition 3, while Composition 2 shows a much smaller floc size increase. The less drastic shift in coacervate floc size of the Composition 2, even at higher NaCl concentrations, is attributed to the lower contribution of D4/D5 to the composition vis-à-vis Composition 3, which has about three times higher level of D4/D5 to that of Composition 2.

TABLE 5

Effect of D4/D5 concentration on salt concentration needed to achieve target viscosity

| Silicone Emulsion | Comp 1 | Comp 2 | Comp 3 | Comp 5 |
|---|---|---|---|---|
| Silicone type | — | dimethiconol | dimethiconol | dimethicone |
| Silicone Particle Size (nm) | — | 100 | 30 | 28,000 |
| Silicone molecular weight (g/mol) | — | 150,000 | 70,000 | 200,000 |
| *Percent D4/D5 | — | 0.5/.2 | 1.6/.4 | <1.0/<2.0 |
| Percent NaCl to achieve 9000 cPs at 2 s$^{-1}$ | 0.5 | 0.5 | 1.5 | 0.3 |
| Percent coacervate floc greater than 20 microns | 3.0 | 8.6 | 14.5 | 4.4 |
| Coacervate Squeeze Flow Viscosity in Pa·s at 100 s-1 | 105.6 | 39.2 | 61 | 57.3 |
| Mean consumer acceptance rating and conclusion (on scale of 1 to 100) | — | Good (80) | Fair (60) | — |

*D4 is octamethylcyclotetrasiloxane, percentage based on the weight of the emulsion.
*D5 is decamethylcyclotetrasiloxane, percentage based on the weight of the emulsion.

In Table 5, one observable effect of the reduced salt concentration is the retention of smaller floc size, as indicated by the low percentage of coacervate particles larger than 20 microns. Unexpectedly, the smaller floc size, in conjunction with a lower coacervate squeeze flow viscosity, provides a synergistic effect and thereby affords an increased consumer acceptance rating. Notably, when the D4 content is about 0.5 wt %, exceptionally good consumer acceptance was achieved.

Clauses

The following clauses are part of the description.

1. A personal care composition comprising:
   a) an anionic surfactant;
   b) a cationic conditioning polymer selected from at least one of:
      i) a cationic guar polymer, wherein the cationic guar polymer has a weight average molecular weight of less than 1 million g/mol, or less than 900 thousand g/mol, or from about 150 thousand to about 800 thousand g/mol, and wherein the cationic guar polymer has a charge density of from 0.1 meq/g to 2.5 meq/g; or
      ii) a cationic copolymer of an acrylamide monomer and a cationic monomer, wherein the copolymer has a charge density of from 1.0 meq/g to 3.0 meq/g; and
   c) a silicone emulsion comprising an insoluble polysiloxane having a general formula of $R^1$—[O—$SiR_2$]$_n$—$OR^1$, wherein n is an integer, R is a substituted or unsubstituted $C_1$ to $C_{10}$ alkyl or aryl, and $R^1$ is a hydrogen or a substituted or unsubstituted $C_1$ to $C_{10}$ alkyl or aryl, wherein the insoluble polysiloxane has an average molecular weight within the range from 50,000 to 500,000 g/mol, or from about 60,000 to about 400,000, or from about 75,000 to about 300,000, or from about 100,000 to about 200,000, and wherein the insoluble polysiloxane has an average particle size within the range from 30 nm to 10 microns, or from 40 nm to 5 micron, or from 50 nm to 1 micron, or from 75 nm to 500 nm; and wherein a total content of a cyclic polysiloxane having a general formula:

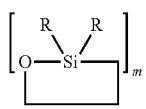

is present in the silicone emulsion in an amount less than 2.5 wt % based on the total weight of the insoluble polysiloxane and the cyclic polysiloxane, wherein R is as defined above, and wherein m is 4 or 5.

2. The personal care composition of clause 1, wherein the composition is capable of forming coacervate particles upon dilution with water, and wherein if the personal care composition is diluted 1 in 50 with water, the percentage of the coacervate particles with a floc size of greater than 20 micron is from 1% to 60%, or from 1% to 50%, or from 1% to 40%, or from 1% to 30%, or from 2% to 25%; or from 5% to 20%, or from 5% to 15%.

3. The personal care composition according to any of the preceding clauses, wherein the coacervate particles have a squeeze flow viscosity of from 1 Pa·s to 100 Pa·s, or from 1 Pa·s to 80 Pa·s, or from 2 Pa·s to 60 Pa·s, or from 3 Pa·s to 50 Pa·s, or from 4 Pa·s to 40 Pa·s, or from 5 Pa·s to 30 Pa·s, or from 10 Pa·s to 20 Pa·s, measured at 25° C. with a TA AR2000 rheometer at a 100 s$^{-1}$.

4. The personal care composition according to any of the preceding clauses, wherein R is methyl and $R^1$ is hydrogen.

5. The personal care composition according to any of the preceding clauses, wherein m is 4 and the total content of a cyclic polysiloxane is less than 1.5 wt %, or less than 1.0 wt %.

6. The personal care composition according to any of the preceding clauses, wherein the insoluble polysiloxane is present in the composition in an amount within the range from 0.1 wt % to 3 wt %, or from 0.2 wt % to 2.5 wt %, or from 0.4 wt % to 2.0 wt %, or from 0.5 wt % to 1.5 wt %, based on the total weight of the composition.

7. The personal care composition according to any of the preceding clauses, wherein the silicone emulsion has a viscosity up to 500,000 cPs, or from 100,000 cPs to 200,000 cPs, measured at 30° C. with a Brookfield viscosimeter with spindle 6 at 2.5 rpm.

8. The personal care composition according to any of the preceding clauses, wherein the insoluble polysiloxane has an average particle size ($D_{50}$) within the range from 50 nm to 150 nm.

9. The personal care composition according to any of the preceding clauses, further comprising at least one of:
(a) an anti-dandruff active;
(b) a cosmetically acceptable carrier;
(c) a benefit agent.

10. The personal care composition according to any of the preceding clauses, wherein the personal care composition comprises an anti-dandruff active, and wherein the anti-dandruff active is selected from the group consisting of: antimicrobial actives, pyridinethione salts, azoles, selenium sulfide, particulate sulfur, keratolytic acid, salicylic acid, octopirox (piroctone olamine), coal tar, and mixtures thereof.

11. The personal care composition according to any of the preceding clauses, further comprising a zinc-containing layered material selected from the group consisting of basic zinc carbonate, zinc carbonate hydroxide, hydrozincite, zinc copper carbonate hydroxide, aurichalcite, copper zinc carbonate hydroxide, rosasite, phyllosilicate containing zinc ions, layered double hydroxide, hydroxy double salts, and mixtures thereof.

12. The personal care composition according to any of the preceding clauses, wherein the personal care composition comprises the cationic guar polymer and the cationic copolymer.

13. Use of the personal care composition, according to any of the preceding clauses, for treating hair, or for achieving improved hair feel.

14. A method for treating hair, or for achieving improved hair feel, wherein the method comprises applying to hair the personal care composition according to any of clauses 1 to 12.

15. A method of making a personal care composition comprising an anionic surfactant, a cationic conditioning polymer, and a silicone emulsion, the method comprising:
(i) combining the anionic surfactant and the cationic conditioning polymer in water, wherein the cationic conditioning polymer is selected from at least one of:
  a cationic guar polymer, wherein the cationic guar polymer has a weight average molecular weight of less than 1 million g/mol, and wherein the cationic guar polymer has a charge density of from 0.1 meq/g to 2.5 meq/g; or
  a cationic copolymer of an acrylamide monomer and a cationic monomer, wherein the copolymer has a charge density of from 1 meq/g to 3 meq/g; and
(ii) combining a silicone emulsion and an aqueous composition that includes a product of step (i) to form the personal care composition, the silicone emulsion comprising an insoluble polysiloxane having a general formula of $R^1$—[O—$SiR_2$]$_n$—$OR^1$, wherein n is an integer, R is a substituted or unsubstituted $C_1$ to $C_{10}$ alkyl or aryl, and $R^1$ is a hydrogen or a substituted or unsubstituted $C_1$ to $C_{10}$ alkyl or aryl, wherein the insoluble polysiloxane has an average molecular weight within the range from 50,000 to 500,000 g/mol, or from about 60,000 to about 400,000, or from about 75,000 to about 300,000, or from about 100,000 to about 200,000, and wherein the insoluble polysiloxane has an average particle size within the range from 30 nm to 10 microns, or from 40 nm to 5 micron, or from 50 nm to 1 micron, or from 75 nm to 500 nm; and wherein a total content of a cyclic polysiloxane having a general formula

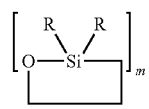

is present in the silicone emulsion in an amount less than 2.5 wt % based on the total weight of the insoluble polysiloxanes and the cyclic polysiloxane, wherein R is as defined above, wherein m is 4 or 5.

16. A method of making a personal care composition according to clause 15, wherein the personal care composition is capable of forming coacervate particles upon dilution with water, and wherein if the composition is diluted 1 in 50 with water, the percentage of the coacervate particles with a floc size of greater than 20 micron is from 1% to 60%, or from 1% to 50%, or from 1% to 40%, or from 1% to 30%, or from 2% to 25%; or from 5% to 20%, or from 5% to 15

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A personal care composition comprising:
   a) an anionic surfactant;
   b) a cationic conditioning polymer selected from at least one of
      i) a cationic guar polymer, wherein the cationic guar polymer has a weight average molecular weight of less than about 1 million g/mol, and wherein the cationic guar polymer has a charge density of from about 0.1 meq/g to about 2.5 meq/g; or
      ii) a cationic copolymer of an acrylamide monomer and a cationic monomer, wherein the copolymer has a charge density of from about 1.0 meq/g to about 3.0 meq/g; and
   c) i) a silicone emulsion comprising an insoluble polysiloxane having a general formula of $R^1$—[O—$SiR_2$]$_n$—$OR^1$, wherein n is an integer, R is a substituted or unsubstituted $C_1$ to $C_{10}$ alkyl or aryl, and $R^1$ is a hydrogen or a substituted or unsubstituted $C_1$ to $C_{10}$ alkyl or aryl, wherein the insoluble polysiloxane has an average molecular weight within the range from about 50,000 to about 500,000 g/mol, and an average particle size within the range from about 30 nm to about 10 μm, wherein a total content of a cyclic polysiloxane having a general formula:

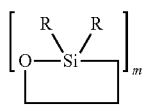

is present in the silicone emulsion in an amount less than about 2.5 wt % based on the total weight of the insoluble polysiloxane and the cyclic polysiloxane, wherein R is as defined above, wherein m is 4 or 5, and
   ii) wherein the composition forms coacervate particles upon dilution with water, and wherein a percentage of the coacervate particles with a floc size of greater than about 20 micron is from about 1% to about 40% upon dilution with water.

2. The personal care composition of claim 1, wherein the coacervate particles have a squeeze flow viscosity of from about 1 Pa·s to about 100 Pa·s.

3. The personal care composition of claim 1, wherein R is methyl and $R^1$ is hydrogen.

4. The personal care composition of claim 3, wherein m is 4 and the total content of a cyclic polysiloxane is less than about 1.5 wt %.

5. The personal care composition of claim 3, wherein m is 4 and the total content of a cyclic polysiloxane is less than about 1.0 wt %.

6. The personal care composition of claim 1, wherein the insoluble polysiloxane is present in the composition in an amount within the range from about 0.1 wt % to about 3 wt % based on the total weight of the composition.

7. The personal care composition of claim 1, wherein the silicone emulsion has a viscosity up to about 500,000 cPs.

8. The personal care composition of claim 7, wherein the viscosity is within the range from about 100,000 cPs to about 200,000 cPs.

9. The personal care composition of claim 1, wherein the insoluble polysiloxane has an average particle size ($D_{50}$) within the range from about 50 nm to about 150 nm.

10. The personal care composition of claim 1, further comprising a benefit agent.

11. The personal care composition of claim 1, further comprising:
    a) an anti-dandruff active;
    b) a cosmetically acceptable carrier.

12. The personal care composition of claim 11, wherein the anti-dandruff active is selected from the group consisting of antimicrobial actives, pyridinethione salts, azoles, selenium sulfide, particulate sulfur, keratolytic acid, salicylic acid, octopirox (piroctone olamine), coal tar, and mixtures thereof.

13. The personal care composition of claim 1, further comprising a zinc-containing layered material selected from the group consisting of basic zinc carbonate, zinc carbonate hydroxide, hydrozincite, zinc copper carbonate hydroxide, aurichalcite, copper zinc carbonate hydroxide, rosasite, phyllosilicate containing zinc ions, layered double hydroxide, hydroxy double salts, and mixtures thereof.

14. A method of achieving improved hair feel, comprising applying to hair the composition of claim 1.

15. The method of claim 14, wherein the silicone emulsion has a viscosity up to about 500,000 cPs.

16. The method of claim 14, wherein the composition comprises the cationic guar polymer and the cationic copolymer.

17. The method of claim 14, wherein the composition further comprises an anti-dandruff active.

18. The method of claim 14, wherein the anti-dandruff active is selected from the group consisting of antimicrobial actives, pyridinethione salts, azoles, selenium sulfide, particulate sulfur, keratolytic acid, salicylic acid, octopirox (piroctone olamine), coal tar, and mixtures thereof.

19. The method of claim 14, wherein the composition further comprises a zinc-containing layered material selected from the group consisting of basic zinc carbonate, zinc carbonate hydroxide, hydrozincite, zinc copper carbonate hydroxide, aurichalcite, copper zinc carbonate hydroxide, rosasite, phyllosilicate containing zinc ions, layered double hydroxide, hydroxy double salts, and mixtures thereof.

20. A method of making the composition of claim 1, comprising an anionic surfactant, a cationic conditioning polymer, and a silicone emulsion, the method comprising:
(i) combining the anionic surfactant and the cationic conditioning polymer in water, wherein the cationic conditioning polymer is selected from at least one of
a cationic guar polymer, wherein the cationic guar polymer has a weight average molecular weight of less than about 1 million g/mol, and wherein the cationic guar polymer has a charge density of from about 0.1 meq/g to about 2.5 meq/g; or
a cationic copolymer of an acrylamide monomer and a cationic monomer, wherein the copolymer has a charge density of from about 1 meq/g to about 3 meq/g; and
(ii) combining a silicone emulsion and an aqueous composition that includes a product of step (i) to form the personal care composition, the silicone emulsion comprising an insoluble polysiloxane having a general formula of $R^1$—[O—$SiR_2$]$_n$—$OR^1$, wherein n is an integer, R is a substituted or unsubstituted $C_1$ to $C_{10}$ alkyl or aryl, and $R^1$ is a hydrogen or a substituted or unsubstituted $C_1$ to $C_{10}$ alkyl or aryl, wherein the insoluble polysiloxane has an average molecular weight within the range from about 50,000 to about 500,000 g/mol, and an average particle size within the range from about 30 nm to about 10 μm, and wherein a total content of a cyclic polysiloxane having a general formula

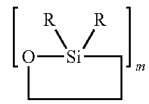

is present in the silicone emulsion in an amount less than 2.5 wt % based on the total weight of the insoluble polysiloxanes and the cyclic polysiloxane, wherein R is as defined above, wherein m is 4 or 5, and
wherein the composition forms coacervate particles upon dilution with water, wherein the coacervate particles have a squeeze flow viscosity of from about 1 Pa·s to about 100 Pa·s, and wherein a percentage of the coaceryate particles with a floc size of greater than about 20 micron is from about 1% to about 60%.

* * * * *